(12) United States Patent
Chung et al.

(10) Patent No.: US 11,397,140 B2
(45) Date of Patent: Jul. 26, 2022

(54) METHODS FOR REVERSIBLE AND TUNABLE TISSUE MAGNIFICATION

(71) Applicant: Massachusetts Institute of Technology, Cambridge, MA (US)

(72) Inventors: Kwanghun Chung, Cambridge, MA (US); Taeyun Ku, Cambridge, MA (US); Justin Mark Swaney, Cambridge, MA (US); Jeong Yoon Park, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 327 days.

(21) Appl. No.: 16/093,204

(22) PCT Filed: Apr. 28, 2017

(86) PCT No.: PCT/US2017/030285
§ 371 (c)(1),
(2) Date: Oct. 12, 2018

(87) PCT Pub. No.: WO2017/190101
PCT Pub. Date: Nov. 2, 2017

(65) Prior Publication Data
US 2019/0145868 A1 May 16, 2019

Related U.S. Application Data

(60) Provisional application No. 62/330,018, filed on Apr. 29, 2016.

(51) Int. Cl.
| | | |
|---|---|---|
| *G01N 1/30* | (2006.01) | |
| *G01N 33/569* | (2006.01) | |
| *G01N 1/36* | (2006.01) | |
| *G01N 1/38* | (2006.01) | |

(52) U.S. Cl.
CPC ......... *G01N 1/30* (2013.01); *G01N 33/56966* (2013.01); *G01N 1/36* (2013.01); *G01N 1/38* (2013.01)

(58) Field of Classification Search
None
See application file for complete search history.

(56) References Cited

U.S. PATENT DOCUMENTS

| 4,320,157 A | 3/1982 | Von Hagens | |
|---|---|---|---|
| 5,431,952 A | 7/1995 | Ocello | |
| 5,578,452 A | 11/1996 | Shi et al. | |
| 10,416,116 B2 | 9/2019 | Chung et al. | |
| 2013/0137094 A1 | 5/2013 | Espina et al. | |
| 2015/0087001 A1 | 3/2015 | Gradinaru et al. | |
| 2015/0144490 A1* | 5/2015 | Deisseroth | G01N 27/44747 204/461 |
| 2016/0123854 A1 | 5/2016 | Gradinaru et al. | |
| 2017/0219465 A1 | 8/2017 | Deisseroth et al. | |
| 2017/0276578 A1* | 9/2017 | Vaughan | G01N 1/30 |
| 2018/0356318 A1 | 12/2018 | Chung et al. | |
| 2021/0348991 A1 | 11/2021 | Chung et al. | |

FOREIGN PATENT DOCUMENTS

| WO | WO 2015/127183 A2 | 8/2015 | |
|---|---|---|---|
| WO | WO-2015127183 A2 * | 8/2015 | ............... G01N 1/36 |
| WO | WO 2016/023009 A1 | 2/2016 | |
| WO | WO 2017/027368 A1 | 2/2017 | |

OTHER PUBLICATIONS

International Search Report and Written Opinion dated Aug. 7, 2017 for Application No. PCT/US2017/030285.
International Preliminary Report on Patentability dated Nov. 8, 2018 for Application No. PCT/US2017/030285.
Murray et al., Simple, scalable proteomic imaging for high-dimensional profiling of intact systems. Cell. Dec. 3, 2015; 163(6):1-16. Supplemental Figures and Supplemental Information pp. 17-35.
Berod et al., Importance of fixation in immunohistochemistry: use of formaldehyde solutions at variable pH for the localization of tyrosine hydroxylase. J Histochem Cytochem. Jul. 1981;29(7):844-50. doi: 10.1177/29.7.6167611.
Chung et al., CLARITY for mapping the nervous system. Nat Methods. Jun. 2013;10(6):508-13. doi: 10.1038/nmeth.2481. Erratum in: Nat Methods. Oct. 2013;10(10):1035.
Chung et al., Structural and molecular interrogation of intact biological systems. Nature. May 16, 2013;497(7449):332-7. doi: 10.1038/nature12107. Epub Apr. 10, 2013.
Dodt et al., Ultramicroscopy: three-dimensional visualization of neuronal networks in the whole mouse brain. Nat Methods. Apr. 2007;4(4):331-6. doi: 10.1038/nmeth1036. Epub Mar. 25, 2007.
Ertürk et al., Three-dimensional imaging of solvent-cleared organs using 3DISCO. Nat Protoc. Nov. 2012;7(11):1983-95. doi: 10.1038/nprot.2012.119. Epub Oct. 11, 2012.
Gleave et al., A method for 3D immunostaining and optical imaging of the mouse brain demonstrated in neural progenitor cells. PLoS One. Aug. 6, 2013;8(8):e72039. doi: 10.1371/journal.pone.0072039.
Hama et al., Scale: a chemical approach for fluorescence imaging and reconstruction of transparent mouse brain. Nat Neurosci. Aug. 30, 2011;14(11):1481-8. doi: 10.1038/nn.2928.
Horiuchi et al., Three-dimensional ultrastructure of the brush border glycocalyx in the mouse small intestine: a high resolution scanning electron microscopic study. Arch Histol Cytol. 2005;68(1):51-6.
Ke et al., SeeDB: a simple and morphology-preserving optical clearing agent for neuronal circuit reconstruction. Nat Neurosci. Aug. 2013;16(8):1154-61. doi: 10.1038/nn.3447. Epub Jun. 23, 2013.

(Continued)

*Primary Examiner* — Emily A Cordas
(74) *Attorney, Agent, or Firm* — Wolf, Greenfield & Sacks, P.C.

(57) ABSTRACT

This disclosure provides methods for producing size-adjustable tissue-hydrogel hybrids or cell-hydrogel hybrids for imaging cellular and subcellular details and system-scale (e.g., tissue or organism level) intercellular connectivity.

12 Claims, 17 Drawing Sheets

(56) References Cited

OTHER PUBLICATIONS

Kim et al., Light microscopy mapping of connections in the intact brain. Trends Cogn Sci. Dec. 2013;17(12):596-9. doi: 10.1016/j.tics.2013.10.005. Epub Nov. 6, 2013.
Kuwajima et al., ClearT: a detergent-and solvent-free clearing method for neuronal and non-neuronal tissue. Development. Mar. 2013;140(6):1364-8. doi: 10.1242/dev.091844.
Leach et al., Crosslinked alpha-elastin biomaterials: towards a processable elastin mimetic scaffold. Acta Biomater. Mar. 2005;1(2):155-64. doi: 10.1016/j.actbio.2004.12.001. Epub Jan. 12, 2005.
Molin et al., A kinetic study of the reaction between glutaraldehyde and horseradish peroxidase. J Histochem Cytochem. Dec. 1978;26(12):1053-6.
Murray et al., Simple, Scalable Proteomic Imaging for High-Dimensional Profiling of Intact Systems. Cell. Dec. 3, 2015;163(6):1500-14. doi: 10.1016/j.cell.2015.11.025.
Renier et al., iDISCO: a simple, rapid method to immunolabel large tissue samples for volume imaging. Cell. Nov. 6, 2014;159(4):896-910. doi: 10.1016/j.cell.2014.10.010. Epub Oct. 30, 2014.
Srinivasan et al., Effect of fixatives and tissue processing on the content and integrity of nucleic acids. Am J Pathol. Dec. 2002;161(6):1961-71.
Tomer et al., Advanced CLARITY for rapid and high-resolution imaging of intact tissues. Nat Protoc. Jul. 2014;9(7):1682-97. doi: 10.1038/nprot.2014.123. Epub Jun. 19, 2014.
Yang et al., Single-cell phenotyping within transparent intact tissue through whole-body clearing. Cell. Aug. 14, 2014;158(4):945-958. doi: 10.1016/j.cell.2014.07.017. Epub Jul. 31, 2014.
Ku et al., Elasticizing tissues for reversible shape transformation and accelerated molecular labeling. Nat Methods. Jun. 2020;17(6):609-613. doi: 10.1038/s41592-020-0823-y. Epub May 18, 2020. PMID: 32424271; PMCID: PMC8056749.

* cited by examiner

METHODS FOR REVERSIBLE AND TUNABLE TISSUE MAGNIFICATION

RELATED APPLICATION

This application is a national stage filing under 35 U.S.C. § 371 of international application number PCT/US2017/030285, filed Apr. 28, 2017 which claims the benefit under 35 U.S.C. § 119(e) of U.S. Provisional Application Ser. No. 62/330,018, filed on Apr. 29, 2016, entitled contents of each of which are incorporated by reference herein.

BACKGROUND

Biological systems such as the brain consist of thousands of distinct cell types forming hundreds of interconnected functional areas[1-5]. Understanding how these diverse cells interact to generate systems-level responses is essential for many fields of biology. The study of such complex interactions may benefit from tools that enable holistic reconstruction of cellular connectivity, molecular details, and fine subcellular architectures of individual cells and their surrounding tissue environment.

Antibody-based proteomic imaging strategies have the potential to provide such multi-scale information[6-10]. Super-resolution imaging of immunolabeled thin tissue sections has been successfully used to reconstruct minute subcellular structures (e.g., neuronal processes and chemical synapses)[11]. Emerging intact tissue clearing techniques preserve the continuity of long-range projects and may allow reconstruction of brain-wide inter-areal connectivity[2,13]. Pioneering multiplexed proteomic imaging tools can provide rich molecular details of individual neurons and may allow reconstruction of their surrounding tissue environment[14-18]. Combined extraction of this multi-scale information might offer new opportunities to define fundamental cell types and study their system-wide complex interactions. Yet, such integrated study remains an unmet goal in biology.

SUMMARY

Provided herein, inter alia, are methods for extracting nanoscale molecular architecture as well as system-level intercellular connectivity from biological samples such as but not limited to a single intact organ. The method is referred to herein as "MAP" (Magnified Analysis of Proteome). MAP preserves both the three-dimensional (3D) proteomic library and organ-wide cellular connectivity within an intact sample-hydrogel hybrid, such as a tissue-hydrogel hybrid, while making it size-adjustable for multi-resolution imaging. The method allows tissues to be expanded linearly at least 4-5 fold relative to their original volume. Such expansion is reversible and thus an end user is able to expand the tissue to a degree desired for a particular imaging application.

Once expanded, the tissue may be probed for the presence and/or location of one or a plurality of proteins. The proteome is an ideal substrate for multi-resolution imaging given the distinct locations and functions of proteins, and the availability of protein detection reagents such as but not limited to an existing large antibody library (close to 100,000 antibodies, corresponding to >70% of the protein-coding genes in humans, currently available)[10]. Significantly, as demonstrated herein, the methods of this disclosure may also include repeated cycles of antibody staining and imaging of the tissue of interest, without significant loss of epitopes. Thus, not only are the tissues expanded linearly but they are also rendered sufficiently robust to tolerate repeated antibody staining and clearing without appreciable effect on epitope quality.

Provided herein are methods for processing and imaging samples such as biological samples including tissues. The methods do not require, special equipment or chemicals. In one exemplary demonstration as described in greater detail herein, these methods were used to process and image a mouse brain hemisphere, thereby allowing reconstruction of long-range cellular projections as well as magnified sub-populations.

The methods generally comprise infusing tissues, whether or not fixed, with hydrogel monomers such as but not limited to acrylamide monomers in order to achieve a high concentration of such hydrogel monomers in the tissue. This may be achieved by incubating the tissue in a high concentration of hydrogel monomers, with or without other fixative such as but not limited to formaldehyde. The high concentration of hydrogel monomers reduces intra- and inter-protein crosslinking during the subsequent hydrogel-tissue hybridization step by quenching reactive methylols that form from amine residues reacting with formaldehyde. If the hydrogel monomer is sufficiently high, then the methylols react with the hydrogel monomers rather than with amines or amides in the same protein or in nearby proteins. Thus, the method reduces the formation of methylene bridges within and between proteins in the tissue. Once the hydrogel-tissue hybridization is complete, the tissue is denatured and expanded to a desired degree. Denaturation may be accomplished by incubating the tissue at high temperature (e.g., 80-95° C.) in the presence of detergent (e.g., 200 mM SDS) for a sufficient period of time. This denaturation step is able to dissociate aggregated proteins from each other as well as denature individual proteins. The denatured and/or dissociated proteins are hybridized to the surrounding hydrogel but not to themselves and thus are able to expand along with the hydrogel. Importantly, the expansion is linear, intending that it occurs to about the same degree in all dimensions or directions. In this way, the expanded tissue maintains the relative position of proteins as compared to the original tissue. The tissue may be expanded to any desired degree, and may be probed and imaged repeatedly with a plurality of antibodies or other affinity based binding partners.

Thus, in one aspect, the disclosure provides a method of producing a size-adjustable tissue-hydrogel hybrid comprising:

(a) perfusing (or incubating or immersing or contacting) a tissue with hydrogel subunits, such as hydrogel monomers, under conditions that minimize inter- and intra-tissue bonding, including inter- and intra-protein bonding, (b) inducing hybridization of the hydrogel subunits and tissue, thereby forming a tissue-hydrogel hybrid, and (c) denaturing biomolecules, such as proteins, and optionally dissociating such biomolecules, thereby forming a size-adjustable tissue-hydrogel hybrid.

In another aspect, the disclosure provides a method of producing a size-adjustable cell-hydrogel hybrid comprising:

(a) incubating cultured cells with hydrogel subunits under conditions that minimize inter- or intra-cellular bonding, (b) inducing hybridization of the hydrogel subunits and cultured cells thereby forming a cell-hydrogel hybrid, and (c) denaturing and/or dissociating biomolecules in the cell-hydrogel hybrid, thereby forming a size-adjustable cell-hydrogel hybrid.

In another aspect, the disclosure provides a method for preserving a tissue comprising (a) perfusing (or incubating or immersing or contacting) a tissue with hydrogel subunits under conditions that minimize inter- or intra-tissue binding, (b) inducing polymerization of the hydrogel subunits under conditions which favor binding of hydrogel subunits to each other or to biomolecules in the tissue and which disfavor binding of biomolecules to each other, and (c) denaturing and/or dissociating biomolecules in the tissue, thereby forming a size-adjustable tissue-hydrogel hybrid.

In another aspect, the disclosure provides a method for preserving a tissue comprising (a) perfusing (or incubating or immersing or contacting) a tissue with hydrogel subunits, (b) inducing polymerization of the hydrogel subunits under conditions which favor binding of hydrogel subunits to each other or to biomolecules in the tissue and which disfavor binding of biomolecules to each other, and (c) denaturing and/or dissociating biomolecules in the tissue, thereby forming a size-adjustable tissue-hydrogel hybrid.

In another aspect, the disclosure provides a method for preserving cultured cells comprising (a) incubating cultured cells with hydrogel subunits under conditions that minimize inter- or intra-cellular binding, (b) inducing polymerization of the hydrogel subunits under conditions which favor binding of hydrogel subunits to each other or to biomolecules in the cells and which disfavor binding of biomolecules to each other, and (c) denaturing and/or dissociating biomolecules in the cells, thereby forming a size-adjustable cell-hydrogel hybrid.

Any of the foregoing methods may further comprise expanding the size-adjustable tissue-hydrogel or cell-hydrogel hybrid by incubating it in an aqueous solution such as a buffer, having salt concentration and osmolality compatible with the tissue.

In some embodiments, the tissue is perfused or the cultured cells are incubated with a solution of hydrogel subunits wherein the concentration of hydrogel subunits ranges from 5-80%, 5-70%, 5-60%, 5-50%, 5-40%, 5-30%, 5-20%, or 5-15%, 10-80%, 10-70%, 10-60%, 10-50%, 10-40%, 10-30%, 10-20%, or 10-15% (w/v). It is to be understood that, unless indicated otherwise, concentrations provided as percentages refer to w/v concentrations. In some embodiments, the tissue is perfused or the cultured cells are incubated with a solution of hydrogel subunits wherein the concentration of hydrogel subunits is about 20%.

In some embodiments, the hydrogel subunits are acrylamide, sodium acrylate, bis-acrylamide, or other acrylic monomers. In some embodiments, the hydrogel subunits are acrylamide and bis-acrylamide (which may act as the crosslinker between hydrogel polymer chains) and sodium acrylate and/or other subunit types may be absent. In some embodiments, the tissue is perfused (e.g., incubated) with (or immersed in) hydrogel subunits and a fixative. In some embodiments, the cultured cells are incubated with (or immersed in) hydrogel subunits and a fixative. In some embodiments, the tissue or cells are incubated with (or immersed in or embedded in) hydrogel subunits in the absence of a fixative or in the absence of a chemical agent that reacts with the biomolecules (e.g., the hydrogel subunits may be incubated with a crosslinker that effects crosslinking only between the hydrogel subunits and the biomolecules). Non-limiting examples of fixatives are formaldehyde and glutaraldehyde, in some embodiments. In some embodiments, the tissue or cultured cells are contacted with paraformaldehyde. In some embodiments, the tissue or cultured cells are not contacted with a fixative as part of the hybridization step. In some embodiments, acrylamide monomers and formaldehyde or glutaraldehyde are used, and optionally they are present in a ratio of 1:1, 2:1, 3:1, 4:1, 5:1, 10:1, 15:1, 20:1, 25:1, 30:1, 35:1, or 40:1. In some embodiments, the biomolecules comprise proteins. In some embodiments, the biomolecules comprise nucleic acids such as DNA and RNA. In some embodiments, the biomolecules comprise proteins and nucleic acids.

In some embodiments, the biomolecules are dissociated and denatured. In some embodiments, the biomolecules are denatured. In some embodiments, the biomolecules are aggregated proteins (or protein complexes) that are dissociated and denatured. In some embodiments, denaturation and optionally dissociation comprises chemical, enzymatic and/or mechanical means. In some embodiments, denaturation and optionally dissociation comprises contacting (e.g., incubating) the tissue-hydrogel or cell-hydrogel hybrid with detergent. In some embodiments, denaturation and optionally dissociation comprises contacting (e.g., exposing) the tissue-hydrogel or cell-hydrogel hybrid to a high temperature. The high temperature may be 60-120° C., 65-110° C., 70-105° C., 75-100° C., 80-95° C., 85-95° C., or 90-95° C. In some embodiments, dissociation comprises sonication (e.g., sonicating the tissue-hydrogel hybrid or the cell-hydrogel hybrid).

In some embodiments, the tissue-hydrogel hybrid or the cell-hydrogel hybrid is reversibly size-adjustable in three dimensions. In some embodiments, reversibly size-adjusting the tissue-hydrogel hybrid or the cell-hydrogel hybrid comprises contacting (e.g., incubating) the tissue-hydrogel hybrid or the cell-hydrogel hybrid with an aqueous solution. Such aqueous solution may comprise a buffering agent, and may have a pH that is compatible with the tissue-hydrogel hybrid or the cell-hydrogel hybrid. The aqueous solution may comprise salt, for example at a concentration that is compatible with the tissue-hydrogel hybrid or the cell-hydrogel hybrid. The aqueous solution may have an osmolality that is compatible with the tissue-hydrogel hybrid or the cell-hydrogel hybrid.

In some embodiments, the tissue is a human tissue. In some embodiments, the cultured cells cultured human cells. In some embodiments, the tissue is an animal tissue. In some embodiments, the cultured cells are cultured animal cells. In some embodiments, the tissue is brain, heart, lung, spinal cord, liver, intestine, or kidney. In some embodiments, the sample comprises cultured cells.

In some embodiments, inducing hybridization comprises introducing a polymerization activator such as but not limited to ammonium persulfate, TEMED, or a combination of ammonium persulfate and TEMED.

In another aspect, the disclosure provides a method of producing a size-adjustable tissue-hydrogel hybrid or a size-adjustable cell-hydrogel hybrid comprising:

(a) fixing a tissue or cultured cells using paraformaldehyde and a low concentration of hydrogel subunits, (b) incubating the fixed tissue or fixed cultured cells with paraformaldehyde, glutaraldehyde and a high concentration of hydrogel subunits, such as hydrogel monomers, under conditions that minimize inter- and intra-tissue bonding, including inter- and intra-protein bonding, (c) reacting the hydrogel subunits with the tissue or the cells, thereby forming a tissue-hydrogel hybrid or a cell-hydrogel hybrid, and (d) incubating the tissue-hydrogel hybrid or the cell-hydrogel hybrid with a detergent at a temperature sufficient to denature biomolecules, such as proteins, and optionally dissociate such biomolecules, thereby forming a size-adjustable tissue-hydrogel hybrid or a size-adjustable cell-hydrogel hybrid.

The hydrogel subunits (or monomers) may be but are not limited to acrylamide. The low concentration of hydrogel subunits may be equal to or less than 5%, including equal to or less than 4%. The high concentration of hydrogel subunits may be equal to or greater than 10%, including equal to or greater than 15%, or equal to or greater than 20%.

In some instances, high concentration of one hydrogel monomer may be used and this may preempt the need for another monomer type. For example, in some instances, a high concentration of acrylamide monomers is used and sodium acrylate monomers are not used. In these instances, the high concentration may be 10% or more, 20% or more, 30% or more, 40% or more, 50% or more, 60% or more, 70% or more, or 80% or more.

In another aspect, the disclosure provides a method of producing a size-adjustable tissue-hydrogel hybrid or a size-adjustable cell-hydrogel hybrid comprising:

(a) incubating a tissue or cultured cells with a fixative such as formaldehyde and/or glutaraldehyde and a high concentration of hydrogel subunits, such as hydrogel monomers, under conditions that minimize inter- and intra-tissue bonding, including inter- and intra-protein bonding or inter- and intra-cell bonding, (b) reacting the hydrogel subunits with the tissue or cultured cells, thereby forming a tissue-hydrogel hybrid or a cell-hydrogel hybrid, and (c) incubating the tissue-hydrogel hybrid or the cell-hydrogel hybrid with detergent at a temperature sufficient to denature biomolecules, such as proteins, and optionally dissociate such biomolecules, thereby forming a size-adjustable tissue-hydrogel hybrid or a size-adjustable cell-hydrogel hybrid.

The hydrogel subunits (or monomers) may be but are not limited to acrylamide. The high concentration of hydrogel subunits may be equal to or greater than 10%, including equal to or greater than 15%, or equal to or greater than 20%. In some embodiments, the tissue or culture cells may be fixed prior to incubation with the hydrogel subunits.

In another aspect, the disclosure provides a method for imaging a size-adjustable tissue-hydrogel hybrid or a size-adjustable cell-hydrogel hybrid comprising:

(a) producing the size-adjustable tissue-hydrogel hybrid or the size-adjustable cell-hydrogel hybrid according to any one of the foregoing methods, (b) contacting the size-adjustable tissue-hydrogel hybrid or the size-adjustable cell-hydrogel hybrid with one or more marker-specific binding partners, and (c) detecting binding of the one or more marker-specific binding partners by obtaining one or more images.

In some embodiments, the method further comprises (d) eluting the one or more marker-specific binding partners from the tissue-hydrogel hybrid or the cell-hydrogel hybrid, and repeating steps (b) and (c). In some embodiments, the method further comprises (d) eluting the one or more marker-specific binding partners from the hybrid, (e) adjusting size of the tissue-hydrogel hybrid or the cell-hydrogel hybrid, and repeating steps (b) and (c). The tissue-hydrogel hybrid or the cell-hydrogel hybrid may be contacted with binding partners, imaged, and cleared of such binding partners, and this process may be repeated any number of times.

In some embodiments, the tissue-hydrogel hybrid or the cell-hydrogel hybrid is not substantially degraded throughout the method. The hybrid may be exposed to binding partners, imaged, and cleared of binding partners, 2, 3, 4, 5, 6, 7, 8, 9, 10 or more times, in some embodiments, and still yield accurate information (e.g., as compared to the results obtained from the first cycle of binding partner exposure and imaging).

In some embodiments, the one or more images are overlaid and aligned to obtain a composite image.

In some embodiments, eluting the marker-specific binding partners comprises contacting the tissue-hydrogel hybrid or the cell-hydrogel hybrid with high temperature and/or detergent. In some embodiments, the temperature used to elute the binding partners is lower than the temperature used to generate the tissue-hydrogel hybrid or the cell-hydrogel hybrid. For example, the temperature used to elute the binding partners may be about 70° C. and the temperature used to hybridize the tissue or cultured cells (via the biomolecules) and the hydrogel subunits may be about 80° C. or higher. Both steps of eluting binding partners and hybridizing tissue or cultured cells and hydrogel subunits may be performed in the presence of a detergent such as SDS.

In some embodiments, the binding partners are antibodies or antigen-binding antibody fragments.

In another aspect, the disclosure provides a composition comprising a tissue-hydrogel hybrid. In some embodiments, the tissue-hydrogel hybrid is size-adjustable, including proportionally size-adjustable. In some embodiments, the tissue-hydrogel hybrid is reversibly size-adjustable. In another aspect, the disclosure provides a composition comprising a cell-hydrogel hybrid. In some embodiments, the cell-hydrogel hybrid is size-adjustable, including proportionally size-adjustable. In some embodiments, the cell-hydrogel hybrid is reversibly size-adjustable.

In another aspect, the disclosure provides a composition comprising a tissue-hydrogel hybrid that is equally size-adjustable in three-dimensions. In another aspect, the disclosure provides a composition comprising a cell-hydrogel hybrid that is equally size-adjustable in three-dimensions.

In some embodiments, the tissue-hydrogel hybrid or the cell-hydrogel hybrid is non-labeled (e.g., it does not comprise an exogenously added binding partner such as an exogenously added antibody or an exogenously added stain such as a nucleic acid binding stain). In some embodiments, the tissue-hydrogel hybrid or the cell-hydrogel hybrid is labeled with one or more marker-specific binding partners.

In another aspect, the disclosure provides a method of producing a size-adjustable tissue-hydrogel hybrid or a size-adjustable cell-hydrogel hybrid comprising:

(a) incubating a fixed tissue or fixed cultured cells with hydrogel subunits, such as hydrogel monomers, (b) polymerizing the hydrogel subunits with each other, thereby forming a non-chemically linked tissue- (or cell-) hydrogel hybrid, and (c) incubating the non-chemically linked tissue- (or cell-) hydrogel hybrid with detergent at a temperature sufficient to denature biomolecules, such as proteins, and optionally dissociate such biomolecules, thereby forming a size-adjustable non-chemically linked tissue-hydrogel hybrid or a size-adjustable non-chemically linked cell-hydrogel hybrid.

In some embodiments, the fixed tissue or fixed cultured cells are incubated with, for example, acrylamide, acrylate (such as sodium acrylate), and bis-acrylamide, in the absence of paraformaldehyde (PFA). In some embodiments, acrylamide is present at a concentration of 10% or more, 20% or more, 25% or more, 30% or more, etc. In some embodiments, acrylate (such as sodium acrylate) is present at a concentration of 5% or more, 10% or more, 15% or more, 20% or more, etc. In some embodiments, bis-acrylamide is absent or present at a concentration of 0.000001% or more, 0.00001% or more, 0.0001% or more, 0.001% or more 0.01% or more, 0.05% or more, 0.1% or more, 0.2% or more, or 0.5% or more, etc. (w/v). In some embodiments, the method results in sample expansion on the order of 1, 2, 3, 4, or 5-fold or more. The method may further comprise incubating the resultant expanded tissue or cell sample with one or more antibodies and imaging the sample.

These and other aspects and embodiments of the invention will be described in greater detail herein.

BRIEF DESCRIPTION OF DRAWINGS

(FIGS. 1A-1 and 1A-2) Comparison of hydrogel-tissue hybridization chemistry, subsequent protein denaturation, and hybrid expansion between low (left column) and high (right column) concentrations of acrylamide (AA) infusion. High-concentration AA prevents intra- and inter-protein crosslinking during the hydrogel-tissue hybridization step by quenching reactive methylols formed from amine residues reacting with formaldehyde as schematically illustrated in the Figure, including the color version of the Figure. Disassembly/dissociation and denaturation of non-crosslinked proteins and protein complexes allows natural expansion of the hybrid. In low-concentration AA (left column), the reactive methylols react with available amine or amide groups within the same protein or adjacent proteins and form methylene bridges as illustrated in the Figure including the color version of the Figure. Such intra- and inter-protein crosslinking prevents complete denaturation of the proteins and/or dissociation of the proteins and thereby limits subsequent tissue expansion. (FIG. 1B) BSA-AA gels fixed in higher AA concentrations showed higher degrees of expansion after denaturation. A single gel made of 4% BSA, 4% paraformaldehyde (PFA), and 4% AA was cut into equal size disks, washed overnight, and post-fixed with 2% glutaraldehyde (GA) or various concentrations of AA and 4% PFA. The gels were denatured at 95° C. in 200 mM SDS solution for 1 h and subsequently incubated in DI water. Representative images of the gels before and after expansion are shown (right panel). One-way ANOVA was performed (***P<0.001). Error bars show SD (n=3) (left panel). (FIG. 1C) Expansion of 1-mm-thick coronal mouse brain slices increased with AA concentration. Mice were perfused with various amounts of AA and sodium acrylate (SA) at a constant AA/SA ratio with 4% PFA in PBS. After sectioning, hydrogels were formed, followed by denaturation and DI water incubation. One-way ANOVA was performed (P<0.001). Error bars show mean±SD (n=6). (FIG. 1D) Average diameter of 1-mm-thick slices relative to the initial diameter after expansion and subsequent shrinkage. Slices were allowed 24 h for both expansion and shrinkage (n=6). (FIG. 1E) Representative photos showing expansion and shrinkage of a 1-mm-thick coronal block. Starting from the top left, the original brain section, the expanded state, and the shrunken state are shown. The length increased about 4.2-fold after expansion and decreased to 1.3-fold the original size after shrinkage. (FIGS. 1F-1H) MAP applied to whole brain and other organ samples. The entire process from perfusion to full expansion took 7 days. Compared with the original organ size (pictures at right bottom corner), the final expansion showed a more than 4-fold increase in length. All scale bars, 5 mm. (FIG. 1I) MAP applied to cerebral organoid. Top, dark field images; bottom, bright field image. Scale bars. 10 mm.

(FIG. 1A) A total of 50 antibodies were tested on MAP-processed mouse brain sections and PFA-fixed control tissues (see Table 1). 43 of 50 antibodies were compatible with MAP, and 30 of 32 target molecules were successfully labeled. (FIG. 2B) Representative images showing morphological details of parvalbumin (PV), calbindin (CB), and calretinin (CR) positive cortical neurons. (FIGS. 2C-2D) 3D rendering of fine cytoskeletal structures visualized by neurofilament protein staining: neurofilament heavy unit (NF-H) in a cortical neuron (FIG. 2C), and SMI-312, a pan-axonal marker, and tyrosine hydroxylase (TH) in a subcortical neuron (FIG. 2D). (FIG. 2E) Structural relationship between astrocytes and capillaries visualized with glial fibrillary acidic protein (GFAP), lectin and histone H3 in a subcortical region. (FIG. 2F) 3D rendering of a cortical sample stained with neurofilament medium unit (NF-M) and $GABA_B$ receptor subunit-1 antibodies. The inset shows dendritic spine-associated structures of neurofilaments co-localized with the GABAergic synaptic proteins. (FIG. 2G) Maximum intensity projection (MIP) image showing dendritic spines visualized with a cell type-specific marker, CB. (FIG. 2H) Synaptic structure resolved with a pre-synaptic marker, bassoon, and a glutamatergic post-synaptic marker, PSD95, in a cortical region. White, GFP. The inset highlights the elliptical structures of pre- and post-synaptic proteins distributed at a synaptic junction. (FIG. 2I) Intensity plot along the axis of the synapse in FIG. 2H (dotted line, expanded) showing the separation between pre- and post-synaptic distribution profiles. The lines represent the Gaussian curve fitting. (FIGS. 2J, 2L, and 2M) Additional synaptic markers successfully visualizing molecular synapses in MAP-processed tissues. (FIG. 2J) A glutamatergic pre-synaptic marker (VGluT2) co-localized with bassoon in a cortical region (inset). (FIG. 2K) Comparison of the number of synapses between bassoon and VGluT2 in FIG. 2J (n=3 images). A two-tailed paired t test was performed (*P<0.05). Error bars show mean±SEM. (FIG. 2L) The distribution of pre- (bassoon) and post-synaptic (homer1) markers in a subcortical region. (FIG. 2M) 3D rendering showing the distribution of homer1 clusters in a subcortical region. The images in FIGS. 2F, 2J, and 2M were obtained from samples stained in a second round. The images were obtained with a 25×, 0.95 NA water-immersion objective (FIG. 2B), a 40×, 1.25 NA oil-immersion objective (FIG. 2E) and a 60×, 1.30 NA glycerol-immersion objective (FIGS. 2C, 2D, 2F-H, 2J, 2L, and 2M) with single-photon (1p) excitation (488, 568, 594 and 647 nm).

(FIG. 3A) Connectivity and morphology are preserved in the MAP-processed tissue. Left panel, a 500-μm slice of a mouse brain hemisphere stained with anti-GFP antibody and imaged after expansion and shrinkage. Middle panel, the entire neuronal territory and axon fiber of a cortical pyramidal neuron included within the boxed region in the left panel. The volume was 3D reconstructed with background removal. Right upper panel, images of the same neuron in the middle panel obtained with either a 10×, 0.3 NA objective (before and after expansion) or a 10×, 0.6 NA objective (after shrinkage), showing its morphological details before expansion, after expansion, and after shrinkage. Right lower panel, fine subcellular structures preserved and resolved in the expansion states: dendritic network (right) and dendritic spines (left). (FIG. 3B) Neuronal fibers and cell body (asterisks) morphology visualized using various markers (CR, SMI-312, NF-H, SMI-32, and TH) in different cortical (CR, SMI-312, and NF-H) and subcortical (SMI-312 and TH) regions of a 1-mm hemisphere slice. The inset in the right upper panel shows the ultrastructure observed within a NF-H fiber. The inset in the left panel shows the isolated neuronal cell body and its axon with background removal. (FIG. 3C) Long-range tracing (white line, longer than 3 mm) of an inter-regional TH neurofilament within the rectangular box in FIG. 3B. (FIG. 3D) Subvolume within a square region in FIG. 3B containing dense SMI-312-positive fibers. The line shows a tracing result across the volume, and the left inset visualizes all individual fibers resolved and traced in one of the densest subregions as is apparent from the color version of the Figure. The right box contains closely crossing fibers in a dense region. Depth-color coding of the fibers clearly shows good separation along the z-axis. The intensities of the two fibers closely located in a similar plane are plotted and fitted to Gaussian curves to show their clear separation. Images were obtained using a 10×, 0.6 NA CLARITY-optimized objective (FIG. 3A, before expansion and after shrinkage), a 10×, 0.3 NA water-immersion objective (FIG. 3A, after expansion in right upper panel), a 20×, 0.95 NA water-immersion objective (FIG. 3C), a 63×, 1.30 NA glycerol-immersion objective (FIG. 3B, SMI-312 and TH; FIG. 3D), and a 25×, 0.95 NA water-immersion objective (FIG. 3A, right bottom panels; FIG. 3B, remaining panels) with 1p excitation by 488, 568, and 594 nm.

(FIG. 4A) A mouse brain hemisphere fixed with PFA was embedded into a hydrogel of 40% AA, 10% SA and 0.1% BA without (in the absence of) PFA. The hybrid was cut into 100-μm-thick sections and stained with three antibodies. (FIG. 4B) Six antibodies targeting synaptic proteins were used to compare their specificity and labeling intensity on two types of MAP methods. Top panels show images of MAP samples from a mouse brain perfused by hydrogel subunits and PFA and embedded into a hydrogel in the presence of PFA. Bottom panels show images of MAP samples from a fixed mouse sections embedded into a hydrogel in the absence of PFA. The same laser power and imaging parameters were used for each type of synaptic antibodies for both tissue types.

DETAILED DESCRIPTION

Figures 1, 1A:
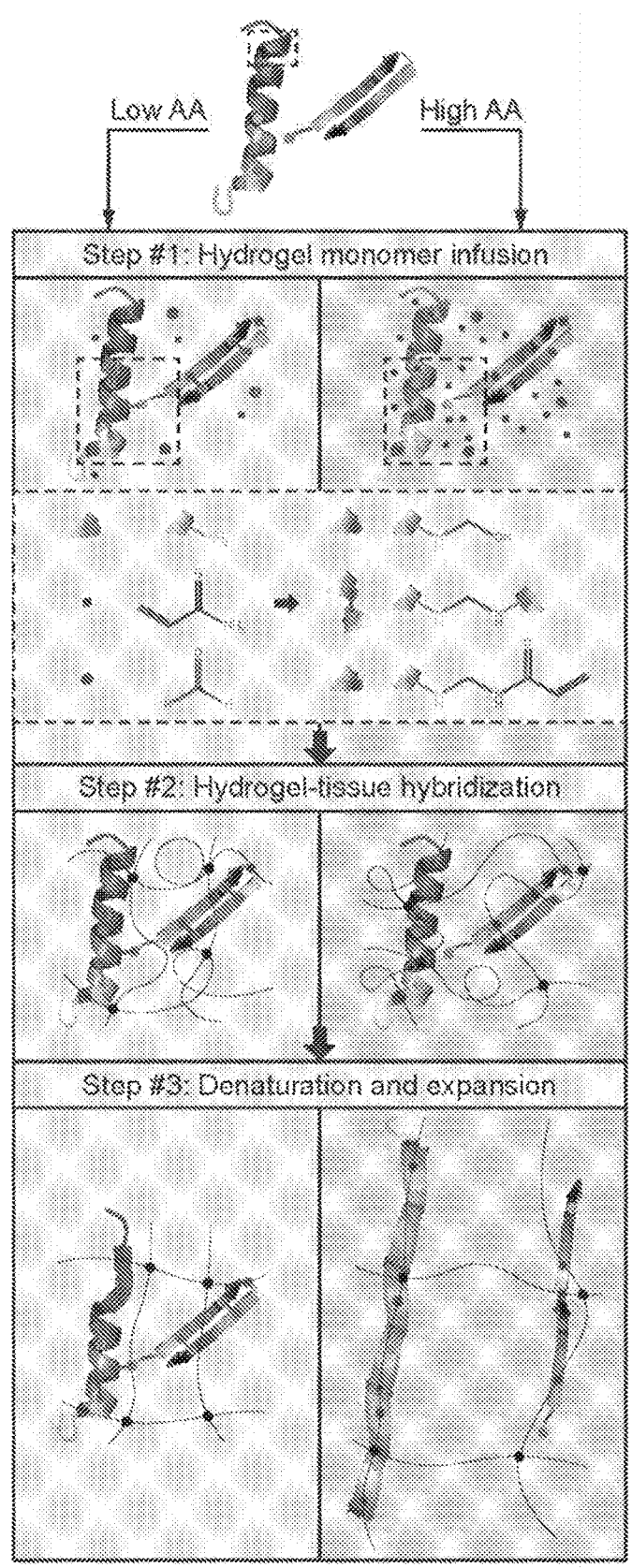
FIGS. 1A-1, 1A-2 and 1B-1I: Magnified and accessible 3D proteome library of whole intact organs.

This disclosure provides, in part, methods for preparing reversibly and uniformly expanding tissue-hydrogel hybrids, as well as the hybrids themselves. In certain methods, the hybrids are generated by preventing or reducing the degree of crosslinking within individual biomolecules or between distinct biomolecules (e.g., proteins) of a tissue. This is accomplished in part by contacting the tissue with an excess of hydrogel subunits (or monomers) such as acrylamide, thereby causing reactive sites in the biomolecules to react with acrylamide rather than other reactive sites in the biomolecules. The tissue typically will have been contacted with a fixative such as formaldehyde and/or will be in contact with formaldehyde at the same time as the high concentration of hydrogel monomers. Thus, in some instances, the tissue is fixed prior to contact with the hydrogel subunits, or it is fixed at the same time as it is in contact with the hydrogel subunits. The resultant tissue-hydrogel hybrids have a number of applications including study of the proteome of the tissue, as described in greater detail herein.

The methods provided herein can be used to analyze and extract nanoscale molecular architecture as well as system-level intercellular connectivity from biological samples such as but not limited to a single intact organ. The methods are referred to herein as "MAP" (Magnified Analysis of Proteome). MAP preserves both the three-dimensional (3D) proteomic library and organ-wide cellular connectivity within an intact sample-hydrogel hybrid, such as a tissue-hydrogel hybrid, while making it size-adjustable for multi-resolution imaging. The method allows tissues to be expanded linearly at least 4-5 fold relative to their original volume. Such expansion is reversible and thus an end user is able to expand the tissue to a degree desired for a particular imaging application.

Once expanded, the tissue may be probed for the presence and/or location of one or a plurality of proteins. The proteome is an ideal substrate for multi-resolution imaging given the distinct locations and functions of proteins, and the availability of protein detection reagents such as but not limited to an existing large antibody library (close to 100,000 antibodies, corresponding to >70% of the protein-coding genes in humans, currently available)[10]. Significantly, as demonstrated herein, the methods of this disclosure may also include repeated cycles of antibody staining and imaging of the tissue of interest, without significant loss of epitopes. Thus, not only are the tissues expanded linearly but they are also rendered sufficiently robust to tolerate repeated antibody staining and clearing without appreciable effect on epitope quality.

Provided herein are methods for processing and imaging samples such as biological samples including tissues. The methods do not require, special equipment or chemicals. In one exemplary demonstration as described in greater detail herein, these methods were used to process and image a mouse brain hemisphere, thereby allowing reconstruction of long-range cellular projections as well as magnified subpopulations.

The invention provides, inter alia, a method for producing a size-adjustable tissue-hydrogel hybrid. The size-adjustable tissue-hydrogel hybrids are formed from tissues including but not limited to animal and human tissues. The tissues so preserved are rendered size-adjustable for multi-resolution imaging. Generally, the method comprises (1) hydrogel subunit perfusion, (2) hydrogel-tissue hybridization, and (3) denaturation and expansion. Hydrogel subunit perfusion ensures uniform chemical diffusion and reaction throughout the tissue sample. Hydrogel subunit perfusion is performed under conditions that minimize inter- and intra-tissue bonding. Hydrogel-tissue hybridization forms bonds between hydrogel subunits and other hydrogel subunits or bonds between hydrogel subunits and tissue.

Denaturing and dissociating non-hybridized biomolecules including but not limited to proteins and nucleic acids enables reversible size-adjustment of the tissue-hydrogel hybrid. The tissue-hydrogel hybrid expands or shrinks proportionally in three dimensions. Reversibly size-adjusting the tissue-hydrogel hybrid comprises contacting the tissue-hydrogel hybrid with an aqueous solution, typically a saline solution. The solution may be characterized by its salt concentration and/or osmolality. The method is versatile and, as described in the Examples, was successfully used to process and expand several other organs, including heart, lung, spinal cord, liver, intestine, and kidney.

The Examples demonstrate exemplary processing and imaging of an intact mouse brain that captures system-scale cellular connectivity and fine subcellular architectures. The proteome library is well preserved within the tissue-hydrogel hybrid and visualized using commercially available antibodies. Antibody targets from a wide range of antigens (e.g., membrane proteins, cytoplasmic proteins, nuclear proteins, neurofilament [NF] proteins, and synaptic proteins) were imaged in order to better represent the overall proteomic landscape. Tissue-hydrogel hybrids were compatible with 43 of 50 antibodies, and successfully visualized with 30 of 32 target proteins.

The MAP method allows repeated staining and imaging of the proteome library within a single tissue because imaged probes are eluted and new targets are visualized by relabeling the same tissue using another set of antibodies.

Size-Adjustable Tissue-Hydrogel Hybrids

Provided herein is a method of producing a size-adjustable tissue-hydrogel hybrid comprising perfusing a tissue with hydrogel subunits under conditions that minimize inter- and intra-tissue bonding, inducing hybridization of the hydrogel subunits to each other or to tissue, and denaturing biomolecules and/or dissociating biomolecules.

As used herein, "perfusing a tissue with hydrogel subunits" minimally comprises contacting a tissue with hydrogel subunits for a time and under conditions that allow diffusion of the hydrogel subunits throughout the tissue. Perfusion may be effected in vivo (i.e., while the tissue is still in the organism) or in vitro (or ex vivo) (i.e., after the tissue has been extracted from the organism). Thus, in some embodiments, perfusing a tissue with hydrogel subunits comprises transcardial perfusion. In some embodiments, perfusing a tissue with hydrogel subunits comprises contacting the tissue with a solution of hydrogel subunits in a container. The tissue or cells may be perfused with one or more hydrogel subunits (e.g., acrylamide and bis-acrylamide or acrylamide, acrylate and bis-acrylamide) depending on the embodiment.

In some embodiments, the tissue may be perfused with hydrogel subunits and one or more fixatives sequentially or simultaneously. In some embodiments, fixatives are formaldehyde, paraformaldehyde (which is converted into formaldehyde upon depolymerization), polyepoxy, and glutaraldehyde. In some embodiments, the tissue is perfused with fixatives in the absence of hydrogel subunits.

In some embodiments, perfusion is carried out at low temperature, including but not limited to 4° C., or a temperature ranging from 4–10° C., or from 4° C. to about room temperature, or at room temperature.

As used herein, "hydrogel subunits" are molecules that are capable of binding to each other and/or to tissue to form a hydrogel. In some embodiments, the hydrogel subunits are bound to each other and bound to tissue. In some embodiments, the hydrogel subunits are bound to each other and minimally bound to tissue. In some embodiments, the hydrogel subunits are bound to each other and not bound to tissue. The ability to control whether the hydrogel units bind to each other or to biomolecules depends on the conditions including the type of monomers used, the concomitant presence of fixative such as PFA, etc. or chemical linkers such as MA-NHS, AcX, etc. that serve to crosslink biomolecules to the hydrogel. It will be understood that binding between hydrogel subunits means covalent binding. Such binding may be referred to herein as bonding.

In the context of this disclosure, the hydrogel is a polymer based semi-solid that is capable of swelling in the presence of an aqueous solution. In some embodiments, the hydrogel subunits are acrylamide or sodium acrylate or other acrylic monomers. In some embodiments, the hydrogel subunits are acrylamide and bis-acrylamide and sodium acrylate or other acrylic monomers. In some embodiments, the hydrogel subunits are acrylamide and bis-acrylamide. In some embodiments, the hydrogel subunits are acrylamide and sodium acrylate or other acrylic monomers. In some embodiments, the hydrogel subunits are acrylamide. In some embodiments, the hydrogel subunits are bis-acrylamide and sodium acrylate or other acrylic monomers.

As used herein, "polymerization" refers to covalent bonding of two or more hydrogel subunits (or monomers, as the terms are used interchangeably herein) to each other or to tissue or to cells or to organelles or to biomolecules. Thus, upon polymerization, a subset of hydrogel subunits may be bound to each other, a subset of hydrogel subunits may be bound to tissue, and a subset of hydrogel subunits may be bound to another hydrogel subunit and to tissue. In some embodiments, hydrogel subunits can be dispersed throughout a tissue and then subsequently polymerized. In some embodiments, hydrogel subunit polymerization is induced through the addition of a polymerization initiator. Examples of polymerization initiators include but are not limited to TEMED and thermal initiators. Other polymerization initiators are also possible and those skilled in the art are capable of selecting suitable polymerization initiators based upon the teachings of the specification. The invention is not limited in this respect.

As used herein, "tissue-hydrogel hybrid" refers to a tissue or a fragment thereof bound to hydrogel subunits, thereby forming semi-solid polymer comprising hydrogel subunits bound to each other and/or tissue. When hydrogel subunits are present with fixatives or chemical linkers, such fixatives and chemical linkers crosslink biomolecules with hydrogel subunits and/or hydrogel polymer chains inside a tissue during perfusion and/or incubation, This type of hybrid may be referred to herein as a chemically linked tissue-hydrogel hybrid.

In some embodiments, another type of tissue-hydrogel hybrid is generated, and it is referred to as a non-chemically linked tissue-hydrogel hybrid, intending that the tissue (or biomolecules of the tissue) and hydrogel are not chemically linked to each other (or are minimally linked to each other). In these instances, the resultant hybrid is still capable of expansion (and contraction) although these occur via mechanical or physical forces rather than chemical linkage between the components of the hybrid. In some instances, such hybrids are formed by first fixing tissue and then incubating or embedding such tissue in a solution of hydrogel monomers, without fixatives and chemical linkers that crosslink biomolecules with hydrogel subunits. The hybrid is formed by allowing the hydrogel monomers to form their respective hydrogel through polymerization of each other predominantly (rather than chemical linking of the hydrogel subunits to biomolecules). The hydrogel monomers may be delivered into the tissue prior to polymerization, with the end result that the hydrogel so formed extends into the tissue sample. Various teachings throughout this disclosure relating to chemically linked tissue-hydrogel hybrids may apply equally to these non-chemically linked tissue-hydrogel hybrids, as will be understood by those of ordinary skill.

The methods provided herein leave intact the biological systems of the tissue including but not limited to the proteome, cellular connections, and subcellular structures. In some embodiments, tissue-hydrogel hybrid is non-labeled, intending that it is not bound to a label whether such label is inherently detectable (such as a dye) or non-detectable. In some embodiments and as discussed below in greater detail, the tissue-hydrogel hybrid is labeled, for example with a binding partner such as but not limited to an antibody or antibody fragment. In some embodiments, the tissue-hydrogel hybrid undergoes multiple rounds of binding partner labeling, imaging, and binding partner removal (or destruction, as the case may be) without significant or any appreciable effect on tissue architecture or target antigenicity. For example, the hybrid may be labeled or stained repeatedly with results varying less than 20%, less than 15%, less than 10%, less than 5% or less than 1% from those obtained in the first labeling or staining cycle. Similarly a cell-hydrogel hybrid refers to a cell or a population of cells (such as cultured cells) bound to hydrogel subunits, thereby forming semi-solid polymer comprising hydrogel subunits bound to each other and/or cells. When cells are incubated in hydrogel subunit solution containing fixatives or chemical linkers, such fixatives and chemical linkers crosslink biomolecules with hydrogel subunits and/or hydrogel polymer chains. This type of hybrid may be referred to herein as a chemically linked cell-hydrogel hybrid.

In some embodiments, another type of cell-hydrogel hybrid is generated, and it is referred to as a non-chemically linked cell-hydrogel hybrid, intending that the cells (or biomolecules of the cells) and hydrogel are not chemically linked to each other (or are minimally linked to each other). In these instances, the resultant hybrid is still capable of expansion (and contraction) although these occur via mechanical or physical forces rather than chemical linkage between the components of the hybrid. In some instances, such hybrids are formed by first fixing cells and then incubating or embedding such cells in a solution of hydrogel monomers without fixatives and chemical linkers that crosslink biomolecules with hydrogel subunits. The hybrid is formed by allowing the hydrogel monomers to form their respective hydrogel through polymerization of hydrogel subunits to each other predominantly (rather than chemical linking of the hydrogel subunits to biomolecules). The hydrogel monomers may be delivered into the cells prior to polymerization, with the end result that the hydrogel so formed extends into the cell sample. Various teachings throughout this disclosure relating to chemically linked cell-hydrogel hybrids may apply equally to these non-chemically linked cell-hydrogel hybrids, as will be understood by those of ordinary skill.

The methods provided herein leave intact the biological systems of the cells and/or of the structures formed by such cells (e.g., an in vitro grown tissue or organ or fragment thereof) including but not limited to the proteome, cellular connections, and subcellular structures. In some embodiments, cell-hydrogel hybrid is non-labeled, intending that it is not bound to a label whether such label is inherently detectable (such as a dye) or non-detectable. In some embodiments and as discussed below in greater detail, the cell-hydrogel hybrid is labeled, for example with a binding partner such as but not limited to an antibody or antibody fragment. In some embodiments, the cell-hydrogel hybrid undergoes multiple rounds of binding partner labeling, imaging, and binding partner removal (or destruction, as the case may be) without significant or any appreciable effect on cell architecture or target antigenicity. For example, the hybrid may be labeled or stained repeatedly with results varying less than 20%, less than 15%, less than 10%, less than 5% or less than 1% from those obtained in the first labeling or staining cycle.

The terms tissue-hydrogel hybrid and hydrogel-tissue hybrid are used interchangeably herein. The terms cell-hydrogel hybrid and hydrogel-cell hybrid are used interchangeably herein.

It is to be understood that the term "tissue" is used throughout this disclosure in a non-limiting manner unless otherwise stated. Thus, the various aspects and embodiments of this disclosure that refer to tissue apply equally to tissue fragments, cells including cultured cells, organelles, and naked biomolecules unless otherwise stated.

In some embodiments, the tissue-hydrogel hybrid is size-adjustable. As used herein, "size-adjustable" refers to altering the size of the tissue or tissue fragment proportionally in three dimensions (or in all directions). Thus, once expanded in size, the tissue resembles its original, non-expanded, form with respect to the relative positioning of cells, extracellular components, and/or intracellular components. In other words, a similar degree of expansion occurs in most or all axes through the center of the tissue or sample. Once expanded, the tissue or sample resembles a magnified form of the original tissue or sample. It is not significantly distorted, if distorted at all. The absolute distance between cells, extracellular components, and/or intracellular components may be different as should be clear once the tissue is size-expanded. In some embodiments, the tissue-hydrogel hybrid is reversibly size-adjustable such that it is capable of expanding and shrinking proportionally in three dimensions. In some embodiments, tissue-hydrogel hybrids are size-adjustable up to 4- to 5-fold linearly in three dimensions. In some embodiments, the tissue-hydrogel hybrids are size-adjustable up to 1, 2, 3, 4, 5, 6, 7, 8, 9, 10, 11,12, 13, 14, 15, 16, 17, 18, 19, 20, 25, 30, 40, 50, or 100-fold or more. The difference in expansion between different axes through the tissue or sample (or in different dimensions (x, y, and z) of the tissue or sample) is less than 20%, less than 15%, less than 10%, less than 5%, 4%, 3%, 2%, or 1%.

In some instances a tissue or a cell sample may be double embedded such that it is first embedded into a first hydrogel solution, such as a high acrylamide (e.g., 40-80% acrylamide) and bis-acrylamide (e.g., 0.0001-0.001%) solution and allowed to expand and then it is further embedded into another hydrogel solution (which may be identical to the first solution). In some instances, the first incubation may result in expansion on the order of about 2-3 fold, and such expansion may be increased to 4-5 fold or more after the second incubation. The disclosure therefore contemplates the use of successive incubations in order to achieve the desired expansion.

The tissue-hydrogel hybrid is generated, at least in part, under conditions that minimize inter- and intra-tissue bonding. Inter-tissue bonding refers to bonding between biomolecules in a tissue (e.g., bonding between reactive groups of different biomolecules). Intra-tissue bonding refers to bonding within a biomolecule (e.g., bonding between reactive groups of a single biomolecule). Thus, as used herein, "conditions that minimize inter- and intra-tissue bonding" refers to a condition that minimizes bonding between biomolecules (inter-tissue bonding) and bonding within a biomolecule (intra-tissue bonding). Such conditions may include modulating the concentration of hydrogel subunits. Low concentrations of hydrogel subunits favor reaction between methylols, formed by the reaction of formaldehyde (the fixative) with a protein (the biomolecule), and amide groups within the same or adjacent proteins to form intra- and inter-protein crosslinks, respectively. High concentrations of hydrogel subunits, on the other hand, favor reaction between the methylols and the excess hydrogel subunits, thereby effectively preventing intra-protein crosslinking, inter-protein crosslinking, and/or nucleic acid crosslinking, and instead tethering the proteins or nucleic acids to the hydrogel subunits. The amount of hydrogel subunits used may vary, as discussed above. It may range from 10-60%, 10-50%, 10-40%, 10-30%, 10-25%, 10-20%, or 10-15% (weight/volume).

As used herein, "hybridization" refers to the binding of a biomolecule to a first hydrogel subunit. A biomolecule conjugated to a first hydrogel subunit may then be conjugated to a second hydrogel subunit. In this way, a tissue-hydrogel or cell-hydrogel hybrid is formed that comprises a plurality of covalent bonds between biomolecules and hydrogel subunits. Alternatively, or in addition to, a non-chemically linked tissue-hydrogel or a non-chemically linked cell-hydrogel hybrid is formed that comprises a plurality of covalent bonds between hydrogel subunits with minimal to no binding between hydrogel subunits and biomolecules.

As used herein, "non-hybridized" refers to hydrogel subunits or tissue not bound to each other. As used herein, "hybrid" refers to a composition comprising hydrogel subunits bonded to tissue, tissue fragment, cell, organelle or biomolecule. The hydrogel subunits may be chemically bound to and/or physically integrated into tissue, tissue fragment, cell, organelle or biomolecule. In some embodiments, a tissue-hydrogel hybrid is a three-dimensional product formed upon covalent binding of hydrogel monomers to biomolecules in the tissue, and it comprises a network or plurality of covalent bonds between biomolecules in the tissue and hydrogel subunits.

In some embodiments, a non-chemically linked tissue-hydrogel hybrid is a three-dimensional product formed upon covalent binding of hydrogel monomers to each other, and it comprises a network or plurality of covalent bonds between hydrogel monomers with minimal to no binding between hydrogel subunits and biomolecules.

In some embodiments, a cell-hydrogel hybrid is a three-dimensional product formed upon covalent binding of hydrogel monomers to biomolecules in (or on) one or more cells, and it comprises a network or plurality of covalent bonds between biomolecules in (or on) the cell(s) and hydrogel subunits.

In some embodiments, a non-chemically linked cell-hydrogel hybrid is a three-dimensional product formed upon covalent binding of hydrogel monomers to each other, and it comprises a network or plurality of covalent bonds between hydrogel subunits with minimal to no binding between hydrogel subunits and biomolecules.

In the absence of biomolecules, the hydrogel subunits covalently bond to each other, thereby forming a hydrogel that is not a hybrid. In other words, the term hybrid is intended to denote the presence of tissue and cell with a hydrogel.

As used herein, "biomolecules" refers to molecules present in the tissue. Biomolecules include but are not limited to proteins, nucleic acids, lipids, and carbohydrates, and metabolites. Non-limiting examples of proteins include enzymes, membrane proteins, secreted proteins, and transcription factors. In some embodiments, biomolecules in the tissue-hydrogel hybrid may be denatured and/or dissociated from each other in the tissue-hydrogel hybrid. The biomolecules may be endogenous biomolecules. Endogenous biomolecules are biomolecules naturally present in the tissue and these may be extracellular or intracellular biomolecules, or they may be membrane-bound biomolecules. The methods provided herein contemplate that any of these biomolecules may be chemically conjugated to hydrogel subunits and in doing so a variety of hydrogel hybrids may be formed including tissue-hydrogel hybrids, cell-hydrogel hybrids, organelle-hydrogel hybrids, and biomolecule-hydrogel hybrids. The methods provided herein further contemplate that any of these biomolecules may be minimally or not at all chemically conjugated to hydrogel subunits and in doing so a variety of hydrogel hybrids may be formed including tissue-hydrogel hybrids, cell-hydrogel hybrids, organelle-hydrogel hybrids, and biomolecule-hydrogel hybrids. The tissue, tissue fragments, cells, or biomolecules to be manipulated according to the methods provided herein may be samples obtained from an in vivo source (e.g., tissue biopsy from a subject) or they may be obtained from an in vitro source (e.g., a cell culture, including a three-dimensional cell culture, including an organ culture, including a synthetic organ generated in vitro, and the like).

In some embodiments, the methods for preserving a tissue further comprise a step of denaturing and/or dissociating biomolecules in the tissue. Denaturing a biomolecule refers to breaking a bond (covalent or non-covalent) within the biomolecule, thereby degrade or destroy its conformation such as a secondary, tertiary, or quaternary conformation, in whole or in part. Denaturation typically does not impact the primary structure of the biomolecule. Thus, for example the peptide backbone of a denatured protein remains intact. Dissociation of a biomolecule refers to breaking a bond (covalent or non-covalent) between one biomolecule and other entity, such as another biomolecule. Thus for example this step of the process may result in two or more biomolecules being physically separated from each other, such as two or more proteins in a protein complex.

Biomolecules may be denatured and/or dissociated in a number of ways, dependent on the nature of the biomolecule. Denaturing and/or dissociation may be chemical, enzymatic and/or mechanical denaturing and/or dissociation. For example, biomolecules that are proteins or nucleic acids may be denatured through contact with a denaturant such as but not limited to a detergent. Non-limiting examples of detergents include lauryl sulfates such as sodium dodecyl sulfate, ammonium lauryl sulfate, and potassium lauryl sulfate. In some embodiments, the detergent is an anionic detergent such as alkylbenzenesulfonates. In some embodiments, the detergent is a cationic detergent such as a quaternary ammonium detergent. In some embodiments, the detergent is a non-ionic detergent such as ethoxylates such as TWEEN® Tween and TRITON® Triton. In some embodiments, the detergent is sodium dodecyl sulfate (SDS). Other detergents or other chemicals are also possible and those skilled in the art would be capable of selecting suitable detergents based upon the teachings of the specification.

In some embodiments, denaturing and/or dissociating biomolecules comprises incubating the tissue-hydrogel hybrid at a high temperature. In some embodiments, denaturing and/or dissociating with high temperature comprises a temperature of 60-120° C., including any temperature and any temperature range there between including for example 65-120° C., 70-120° C., 75-120° C., 80-120° C., 85-120° C., 90-120° C., 100-120° C., and 110-120° C.; and 60-120° C., 60-110° C., 60-100° C., 60-90° C., 60-80° C., and 60-70° C.; and 65-95° C., 70-95° C., 75-95° C., 80-95° C., 85-95° C., and 90-95° C. In some embodiments, dissociating comprises mechanical dissociation and includes sonication and/or electrophoresis.

In some embodiments, denaturing and/or dissociating biomolecules may comprise contact with a denaturant and incubation at a high temperature, simultaneously or consecutively.

In certain embodiments, an acrylamide hydrogel is formed in the absence of acrylate. It has been found in accordance with this disclosure that high concentrations of single monomers such as acrylamide (in the absence of acrylate) can be used to make hydrogels suitable to the methods provided herein. A high concentration may refer to 10% or more, 20% or more, 30% or more, 40% or more, 50% or more, 60% or more, 70% or more, 80% or more, or 10-80%, 20-80%, 30-80%, 40-80%, 50-80%, 60-80%, 70-80%, or 10-70%, 20-70%, 30-70%, 40-70%, 50-70%, 60-70%, or 20-80%, 20-70%, 20-60%, 20-50%, 20-40%, or 20-30%. In some instances, the hydrogel monomers will be self-crosslinking by forming physical crosslinks, particularly if they are high concentration solutions. In other instances, the hydrogel may be formed for example using acrylamide and bis-acrylamide, still in the absence of acrylate. When tissues or cells are hybridized into an acrylamide gel having no acrylate (the term hybridize intending that the biomolecules of the tissues or cells chemically and/or physically bind to the hydrogel monomers), the tissue/cell-hydrogel hybrid expands and its expansion ratio can be modulated by the concentrations of acrylamide and bis-acrylamide and the ratio between these two subunits, and the polymer chain lengths. The size of this type of hybrid can be further adjusted by use of other chemicals instead of ion content, including for example diatrizoic acid, N-methyl-D-glucamine and iodixanol. The advantages of the acrylate-free tissue/cell-hydrogel hybrid include maintaining the same antibody-binding affinity throughout staining and imaging steps, reducing the risk of tissue damage caused by frequent repetition of expansion and shrinkage, preventing the spontaneous shrinkage in DI water by unwanted pH change (e.g., by carbon dioxide in the air) and following movement artifact during a long imaging session, long-term preservation of an expanded sample under mounting, and providing a compatible condition for potential nucleotide binding assay in an expanded MAP sample.

When used, bis-acrylamide may be present at a concentration of 0.000001% or more, 0.00001% or more, 0.0001% or more, 0.001% or more 0.01% or more, 0.05% or more, 0.1% or more, 0.2% or more, or 0.5% or more, etc. (w/v).

As discussed above, another method is provided by this disclosure that involves expansion of a tissue using physical or mechanical forces, as compared to chemical linking and associated chemical forces. This procedure can be carried out on a prefixed tissue (e.g., one that is perfused with a fixative (e.g., PFA) just before performing this method, or one that was fixed and stored for some period of time). The method therefore may use as a substrate a fixed tissue (or cell) sample or it may include as a first step the fixation of a tissue using a fixative such as but not limited to PFA. The method involves delivering hydrogel monomers into a tissue or cell sample and allowing the hydrogel monomers to polymerize to each other, optionally throughout and/or within the tissue or cell sample. The polymerization step does not include fixative or chemical linker and thus the biomolecules of the tissue or cell sample are not chemically linked to the hydrogel (or hydrogel monomers or subunits). The resultant entity is referred to as a non-chemically linked tissue- (or cell-) hydrogel hybrid. In some embodiments, the method further comprises denaturing biomolecules, such as proteins, and optionally dissociating such biomolecules, thereby rendering the hybrid size-adjustable.

The method may first comprise perfusing a tissue (or cell) sample with a fixative (e.g., paraformaldehyde) or it may comprise using a previously prepared, stored fixed tissue or cell sample; After this step, the biomolecules in the tissue or cells can be optionally functionalized by introducing chemicals that can further participate in polymerization of a hydrogel. For example, a hydrogel subunit in a solution with various hydrogel subunit concentration (0-60%) can be attached to each residue of biomolecules in the tissue via fixative or chemical linker. Before polymerizing the hydrogel monomers to each other, any remaining reactive groups formed by the fixative can be optionally quenched. For example, glycine and/or acetamide can be used to quench methylol group formed by PFA.

This second method suppresses chemical hybridization (or linking) between hydrogel subunits and biomolecules but still enables expansion of fixed tissues/cells, including those which have been prepared previously and stored. Also, valuable tissue types such as primate tissue and postmortem human tissue can be obtained using general tissue preservation methods, and a portion of the tissue can be used for this form of MAP (referred to herein as MAP2) expansion or for the first form of MAP described herein (referred to herein as MAP1). The first MAP method (MAP1) aims to reduce or prevent inter- and intra-tissue/cell crosslinking by infusion of hydrogel subunits before the tissue/cell is fixed. In contrast, this second method (MAP2) aims to expand crosslinked biomolecules in the fixed tissue/cell sample without chemical linking of such biomolecules to the hydrogel subunits, and thereby without chemical modification of biomolecules. Thus, the expansion of the tissue or cells in MAP2 relies more on physical or mechanical forces applied to the hydrogel and thus to the tissue or cells. Biomolecules that are less chemically modified due to minimal or no anchoring by polymer chains can maintain their potential to stretch and thereby facilitate expansion of the hybrid.

Tissue Selection

The methods of this disclosure may be used to preserve and image a variety of cells and tissues including but not limited to animal and human tissue. In some embodiments, tissues are derived from humans, companion animals such as dogs or cats, agricultural animals such as cows, sheep and pigs, rodents such as rats or mice, zoo animals, primates such as monkeys, and the like. The tissues may be an organ or a non-organ tissue, including but not limited to brain, lung, liver, kidney, and spinal cord. The tissue may be normal tissue or it may be diseased tissue or it may be tissue suspected of being diseased (e.g., a tissue biopsy obtained for purposes of diagnosing a cancer or other condition). The tissues may be sectioned or whole intact tissues. The Examples demonstrate preservation and multi-resolution imaging of mouse brain tissue sections, whole intact brain, and whole intact heart. Tissues or samples to be manipulated according to the methods provided herein may be obtained from in vivo or in vitro sources and therefore include tissues or cells explanted from a subject as well as tissues or cells grown in vitro. It is to be understood that these methods are exemplary and can be used for a variety of tissues.

Tissue-Hydrogel Hybrid Imaging

Once the tissue-hydrogel hybrid is produced according to the methods provided herein, it may be analyzed for the presence and/or level of one or more markers such as proteins. The presence and/or level of the one or more targets may be determined by contacting the tissue-hydrogel hybrid with marker-specific binding partners. Such marker-specific binding partners may be applied to the tissue-hydrogel hybrid individually or in a group and/or consecutively or simultaneously. Importantly, tissue-hydrogel hybrids prepared according to the methods of this disclosure are able to undergo multiple rounds of marker-specific binding partner labeling, imaging, and marker-specific binding partner removal (or destruction) without significant or any appreciable effect on tissue architecture or target antigenicity.

As used herein, "marker-specific binding partners" may be any molecule or compound capable of binding, preferably specifically, to the target of interest in the tissue-hydrogel hybrid. It should also be possible to remove the binding partner (or destroy the binding partner) in order to facilitate successive rounds of labeling and imaging of the sample. Binding partners may be, without limitation, amino acid based or nucleic acid based. An example of amino acid based binding partners is antibodies and antigen-binding antibody fragments. The antibodies and fragments thereof may be monoclonal antibodies. Another example is a peptide aptamer. An example of nucleic acid based binding partners is aptamers.

As used herein, "antibody" includes full-length antibodies and any antigen binding fragment (e.g., "antigen-binding portion") or single chain thereof. The term "antibody" includes, without limitation, a glycoprotein comprising at least two heavy (H) chains and two light (L) chains interconnected by disulfide bonds, or an antigen binding portion thereof. Antibodies may be polyclonal or monoclonal; xenogeneic, allogeneic, or syngeneic; or modified forms thereof (e.g., humanized, chimeric).

As used herein, "antigen-binding portion" of an antibody, refers to one or more fragments of an antibody that retain the ability to specifically bind to an antigen. The antigen-binding function of an antibody can be performed by fragments of a full-length antibody. Examples of binding fragments encompassed within the term "antigen-binding portion" of an antibody include (i) a Fab fragment, a monovalent fragment consisting of the VH, VL, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VH and VL domains of a single arm of an antibody, (v) a dAb fragment (Ward et al., Nature 341:544 546, 1989), which consists of a VH domain; and (vi) an isolated complementarity determining region (CDR) or (vii) a combination of two or more isolated CDRs, which may optionally be joined by a synthetic linker. Furthermore, although the two domains of the Fv fragment, VH and VL, are coded for by separate genes, they can be joined, using recombinant methods, by a synthetic linker that enables them to be made as a single protein chain in which the VH and VL regions pair to form monovalent molecules (known as single chain Fv (scFv); see, e.g., Bird et al. Science 242:423 426, 1988; and Huston et al. Proc. Natl. Acad. Sci. USA 85:5879-5883, 1988). Such single chain antibodies are also encompassed within the term "antigen-binding portion" of an antibody. These antibody fragments are obtained using conventional techniques known to those with skill in the art, and the fragments are screened for utility in the same manner as are intact antibodies.

As used herein, "peptide aptamer" refers to a molecule with a variable peptide sequence inserted into a constant scaffold protein (see, e.g., Baines I C, et al. Drug Discov. Today 11:334-341, 2006).

As used herein, "nucleic acid aptamer" refers to a small RNA or DNA molecules that can form secondary and tertiary structures capable of specifically binding proteins or other cellular targets (see, e.g., Ni X, et al. Curr Med Chem. 18(27): 4206-4214, 2011).

Typically, these binding partner will themselves be labeled with detectable labels. The detectable labels may be fluorophores. Examples of fluorophores include, without limitation, xanthene derivatives (e.g., fluorescein, rhodamine, Oregon green, eosin and Texas red), cyanine derivatives (e.g., cyanine, indocarbocyanine, oxacarbocyanine, thiacarbocyanine and merocyanine), naphthalene derivatives (e.g., dansyl and prodan derivatives), coumarin derivatives, oxadiazole derivatives (e.g., pyridyloxazole, nitrobenzoxadiazole and benzoxadiazole), pyrene derivatives (e.g., cascade blue), oxazine derivatives (e.g., Nile red, Nile blue, cresyl violet and oxazine 170), acridine derivatives (e.g., proflavin, acridine orange and acridine yellow), arylmethine derivatives (e.g., auramine, crystal violet and malachite green), and tetrapyrrole derivatives (e.g., porphin, phthalocyanine and bilirubin). Other detectable labels may be used in accordance with the present disclosure, such as, for example, gold nanoparticles or other detectable particles or moieties.

When two or more marker-specific binding partners are used simultaneously, it may be preferable to label such marker-specific binding partners with labels that are spectrally distinct (i.e., that can be distinguished from another label being used simultaneously).

Virtually any target of interest may be imaged using the methods provided herein provided a suitable marker-specific binding partner exists. Examples of antibodies used for target labeling are provided in Table 1. The targets may be found in various locations including without limitation at the membrane (e.g., membrane bound), in the cytoplasm, in organelles such as but not limited to the nucleus, and/or at synapses (in the case of neural cells), and the like.

The following Examples are included for purposes of illustration and are not intended to limit the scope of the invention.

EXAMPLES

Example 1

Many biological functions depend on the nanoscale molecular architecture of cells as well as their system-level intercellular connectivity. Here, a method is provided for the extraction of such multi-scale information from a single intact tissue. This method, termed MAP, magnifies whole organs 4-fold linearly while preserving their three-dimensional proteome library and structure. It was discovered that preventing crosslinking within endogenous proteins during hydrogel-tissue hybridization allows for natural expansion upon protein denaturation. The magnified proteome library preserves both fine subcellular details and organ-scale intercellular connectivity. Multiplexed labeling and imaging of these multi-scale properties using off-the-shelf antibodies was demonstrated with an 86% success rate (43/50). With MAP, the physical sample size can be reversibly modulated, enabling proteomic imaging of detailed synaptic architectures as well as broader inter-regional connections. The integrated mapping of biological building blocks within an intact tissue may enable new approaches in the study of complex biological systems.

Materials and Methods
BSA Hydrogel Denaturation and Expansion.

Stock solutions of 40% BSA, 40% AA, 32% PFA, and 1% VA-044 were made and kept on ice throughout the experiment. A 10-ml solution of 4% BSA, 4% AA, 4% PFA, and 0.1% VA-044 was made in PBS. The solution was polymerized under vacuum at 37° C. for 2 h, and the resulting gel was sectioned. Individual gel sections were washed in excess PBS with shaking for 12 h. After washing, four gel sections were placed in 10 ml of each of the following PBS solutions for 4 h at 37° C.: 2% GA, 4% PFA, 4% AA with 4% PFA, and 20% AA with 4% PFA. The gels were washed similarly, massed, photographed, and then incubated in a 200 mM SDS solution with 50 mM sodium sulfite for 1 hour at 95° C. The gels were washed again and incubated in DI water for 12 h. After expansion, the gels were massed and photographed.

General MAP Protocol
i. Perfusion and Hydrogel Embedding.

Thy1-eGFP-M mice (6-8 weeks old) were housed in a reverse 12-h light/dark cycle with unrestricted access to food and water. All experimental protocols were approved by the MIT Institutional Animal Care and Use Committee and the Division of Comparative Medicine and were in accordance with guidelines from the National Institutes of Health. After anesthesia, the mice were first perfused transcardially with a mixture of 5% AA, 0.05% BA, 0.8% SA, 0.1% VA-044, and PBS, followed by a mixture of 4% PFA, 5-30% AA, 0.05% BA, 0.8-5% SA, 0.1% VA-044, and PBS. All solutions were protected from light and kept on ice and before perfusion. Control samples were perfused first with PBS and then with 4% PFA and PBS. The brain and other organs (heart, lung, liver, intestine, kidney and spinal cord) were then harvested and incubated in 20-40 ml of the same fixative solution at 4° C. for 2-3 days and 5-7 h at room temperature with gentle shaking to ensure uniform chemical diffusion and reaction throughout the sample. Following the diffusion and the fixation step, the samples were moved to 5-fold diluted fixative solution containing all the chemicals listed above except VA-044 (VA-044 concentration was kept 0.1%). Hydrogel-tissue hybridization was then performed in situ by incubating the samples under vacuum at 50° C. for 2 h with gentle shaking.

ii. Tissue denaturation.

Hydrogel embedded tissues were incubated in a 200 mM SDS and 50 mM sodium sulfite in PBS solution at room temperature for 1-5 h with gentle shaking. The samples were then incubated at 70-95° C. for 7-60 h depending on the sample size. Whole brain samples, hemispheres, and various whole organs were incubated for 24-48 h at 70° C. followed by 12-24 h at 95° C. For 1-mm-thick brain slices, samples were incubated for 5 h at 70° C. and moved to 95° C. for 1-2 h.

iii. Expansion.

Denatured tissues were incubated in 40-100 ml DI water at room temperature for 12-48 h with gentle shaking. During DI water incubation, the solution was changed every 3-5 h.

Expansion According to Various AA and SA Concentration.

After anesthesia, mice were first perfused transcardially with 5% AA, 0.05% BA, 0.8% SA, 0.1% VA-044 and PBS followed by 4% PFA, 0.05% BA, 0.1% VA-044 and various AA and SA concentration (5% AA+0.8% SA, 10% AA+1.7% SA, 20% AA+3.3% SA, and 30% AA+5% SA) in PBS. Tissues were incubated in 20 ml of the same fixative solution at 4° C. for 2 days and 5 h at room temperature with gentle shaking. After hydrogel-tissue hybridization the samples were incubated in a 200 mM SDS and 50 mM sodium sulfite in PBS solution at 70° C. for 5 h and 95° C. for 2 h with gentle shaking. Denatured tissues were then incubated in 40 ml DI water at room temperature for 12 h with gentle shaking. During DI water incubation, the solution was changed every 3-5 h. Fiji (NIH) was used to measure the size of the expanded samples[32]. The $V_O$ represents the volume before expansion, and V is the volume after expansion.

Shrinkage.

After anesthesia, mice were transcardially perfused with 5% AA, 0.05% BA, 0.8% SA and 0.1% VA-044 in PBS followed by 4% PFA, 30% AA, 0.05% BA, 5% SA, and 0.1% VA-044 in PBS. Before embedding, 1-mm-thick coronal slices (n=6) were made, and hydrogel embedding and expansion were done in the same manner as the above experiment. For shrinkage, expanded tissues were incubated in a customized refractive index matching solution[33] with PBS at room temperature for 24 h with gentle shaking. This shrinkage solution was changed every 12 h. The size of the expanded and shrunken brain slices were measured using Fiji. The $L_0$ is the mean length of original brain, and L is the mean length after expansion and shrinkage.

Customized Refractive Index Matching Solution[33].

A customized refractive index matching solution was made by dissolving 50 g diatrizoic acid, 40 g N-methyl-D-glucamine, and 55 g iodixanol per 100 ml water. This customized refractive index matching solution was used for shrinkage and imaging. For shrinkage, Customized refractive index matching solution in PBS was used. For imaging, expanded samples were incubated in 10 ml of this solution at RT with gentle shaking for 3-5 h prior to imaging. The listed components and their proportions were chosen to adjust the pH and RI for ideal optical clearing and expansion (basic pH with RI near 1.47). All components were considered when optimizing for osmolality. RI was measured using an Abbemat WR/MW automatic multi-wavelength refractometer.

MAP Processing of Cerebral Organoid.

Cerebral organoids were made from stem cells following a previously described protocol33. Organoids were initially fixed in 4% PFA for 15 min, incubated in mixture of 4% PFA, 30% AA, 0.1% BA, 10% SA, 0.1% V–50, and PBS for 24 h at 4° C. followed by 24 h, at RT. Hydrogel embedding, tissue denaturation and expansion were processed similarly to "General MAP protocol".

Cultured Cell Experiment.

For tubulin imaging in HeLa cells, 8-mm round glass coverslips were coated in 0.1% gelatin in ultrapure water (Millipore). Coverslips were placed in a 48-well plate and seeded with 50,000 HeLa cells overnight. To obtain comparable images before and after MAP processing, cells were washed, fixed with 3% PFA+0.1% GA in PBS for 10 min, and switched to a solution of 4% PFA, 30% AA in PBS for 8 hat 37° C. Cells were then placed in 0.1% sodium borohydride for 7 min at RT then incubated in 100 mM glycine for 10 min at RT. Cells were washed and stained with anti-tubulin (Abcam ab6160), ALEXA FLUOR™ Alexa 594 conjugated secondary (Abcam ab150152) and TOTO-1 (Thermofisher Scientific). Cells were mounted in 2,2'-thiodiethanol (Sigma) and imaged with a 63×, 1.3 NA glycerol-immersion objective with the Leica microscope system. Cells were washed extensively and embedded into a MAP hybrid polymer by addition of 20 µL of Cell-MAP solution (20% AA, 7% SA, 0.1% BA, 0.5% TEMED, 0.5% ammonium persulfate in PBS). Ammonium persulfate was added last from a freshly prepared 5% stock solution. Cell-MAP solution was quickly added to the coverslip and left to polymerize for 4-5 min. Gels were peeled off the coverslip using forceps, washed extensively and denatured for 30 min in denaturation buffer at 95° C. Cell-MAP gels were washed extensively, restained with anti-tubulin and TOTO-1 and reimaged.

Immunostaining of Brain Tissue.

For typical staining, MAP-processed 100-500-μm-thick mouse brain coronal slices were incubated with primary antibodies (typical dilution, 1:100) in PBS with 1% (wt/vol) TRITON® Triton X-100 (PBST) at 37° C. for 8-16 h, followed by washing at 37° C. for 1-2 h in PBST three times. The tissue was then incubated with secondary antibodies (typical dilution, 1:100) in PBST at 37° C. for 6-16 h, followed by washing at 37° C. for 1-2 h in PBST three times. For antibody validation of a given antibody, 100-μm-thick PFA-fixed control and MAP-processed samples were stained with the same titer of primary and, if necessary, secondary antibodies overnight in PBST. See Supplementary Table 1 for the list of antibodies used. Destaining for multiplexed labeling, samples were incubated in a denaturation solution 6-16 h at 70° C., and washed with PBST at 37° C. for 1-2 h, three times.

TABLE 1

Antibody summary.

| Target | Vendor[a] | Catalog # | Host species[b] | Clonality[c] | Target size | PFA | MAP |
|---|---|---|---|---|---|---|---|
| Cell type markers | | | | | | | |
| Calbindin | Abcam | ab11426 | Rb | P | Protein | ○ | ○ |
| Calbindin | Abcam | ab82812 | Ms | M | Protein | ○ | X |
| Calretinin | Abcam | ab702 | Rb | P | Protein | ○ | ○ |
| CaMKIIa | Abcam | ab22609 | Ms | M | Protein | ○ | ○ |
| GAD65 | CST | D5G2 | Rb | M | Protein | ○ | ○ |
| GAD65/67 | Millipore | AB1511 | Ms | P | Protein | X | ○ |
| GAD67 | Millipore | MAB5406 | Ms | M | Protein | ○ | ○ |
| GFAP | Abcam | ab48050 | Rb | P | Protein | ○ | ○ |
| GFAP ALEXA FLUOR™ Alexa 488 conjugated) | CST | 3655 | Ms | M | Protein | ○ | ○ |
| Iba1 | Abcam | ab5076 | Gt | P | Protein | ○ | X |
| Iba1 | Wako | 019-19741 | Rb | P | Protein | ○ | X |
| NeuN | Abcam | ab177487 | Rb | M | Protein | ○ | ○ |
| NeuN | BioLegend | 834501 | Ms | M | Protein | ○ | ○ |
| NeuN | CST | 12943 | Rb | M | Protein | ○ | X |
| Parvalbumin | Abcam | ab11427 | Rb | P | Protein | ○ | ○ |
| Parvalbumin | Abcam | ab32895 | Gt | P | Protein | ○ | X |
| TH | Abcam | ab112 | Rb | P | Protein | ○ | ○ |
| TH | Abcam | ab134461 | Ch | P | Protein | ○ | ○ |
| Neurofilament markers | | | | | | | |
| MAP2 | BioLegend | 822501 | Ch | P | Protein | ○ | X |
| MBP | Abcam | ab134018 | Ch | P | Protein | ○ | ○ |
| MBP | Abcam | ab7349 | Rt | M | Protein | ○ | ○ |
| NF-H | Aves | NFH | Ch | P | Protein | ○ | ○ |
| NF-H | CST | 2836 | Ms | M | Protein | ○ | ○ |
| NF-M | Abcam | ab64300 | Rb | P | Protein | ○ | ○ |
| NF-L | Aves | NFL | Ch | P | Protein | ○ | ○ |
| SMI-312 | BioLegend | 837902 | Ms | P | Protein | ○ | ○ |
| SMI-32 | BioLegend | 801704 | Ms | M | Protein | ○ | ○ |
| Neurotransmitters and neuromodulators | | | | | | | |
| Dopamine | Abcam | ab6427 | Rb | P | Small molecules | X | ○ |
| Neuropeptide Y | CST | 11976 | Rb | M | Peptides | ○ | ○ |
| Synaptic proteins | | | | | | | |
| Bassoon | Abcam | ab82958 | Ms | M | Protein | ○ | ○ |
| Bassoon | SYSY | 141003 | Rb | P | Protein | ○ | ○ |
| GABA$_B$R1 | Millipore | AB2256 | GP | P | Protein | ○ | ○ |
| GluR2/3 | Millipore | AB1506 | Rb | P | Protein | ○ | ○ |
| Homer1 | Abcam | ab97593 | Rb | P | Protein | ○ | X |
| Homer1 | SYSY | 160003 | Rb | P | Protein | ○ | ○ |
| PSD95 | CST | D27E11 | Rb | P | Protein | X | ○ |
| PSD95 | CST | D74D3 | Rb | P | Protein | X | ○ |
| PSD95 | NeuroMab | 75-028 | Ms | M | Protein | ○ | ○ |
| Synapsin I | Abcam | ab64581 | Rb | P | Protein | ○ | ○ |
| Synapsin I | CST | D12G5 | Rb | M | Protein | ○ | ○ |
| Synaptophysin | Abcam | ab52636 | Rb | M | Protein | ○ | ○ |
| Synaptophysin | CST | D35E4 | Rb | M | Protein | ○ | ○ |
| SYNPR | Abcam | ab175224 | Rb | M | Protein | ○ | ○ |
| VGluT1 | Abcam | ab104898 | Rb | P | Protein | ○ | ○ |
| VGluT2 | Abcam | ab101760 | Gt | P | Protein | ○ | ○ |

TABLE 1-continued

Antibody summary.

| Target | Vendor[a] | Catalog # | Host species[b] | Clonality[c] | Target size | PFA | MAP |
|---|---|---|---|---|---|---|---|
| Nuclear and other markers | | | | | | | |
| GFP | LT | A10262 | Ch | P | Protein | ○ | ○ |
| GFP ALEXA FLUOR ™ Alexa 594 conjugated) | LT | A21312 | Rb | P | Protein | ○ | ○ |
| GFP ALEXA FLUOR ™ Alexa 647 conjugated) | LT | A31852 | Rb | P | Protein | ○ | ○ |
| Lectin-594 | Vector | DL-1177 | | | Protein | ○ | ○ |
| Histone H3 ALEXA FLUOR ™ Alexa 647 conjugated) | CST | 12230 | Rb | M | Protein | ○ | ○ |
| DAPI | LT | D1306 | | | dsDNA | ○ | X |
| TOTO-1 | LT | T3600 | | | ssDNA | ○ | ○ |

[a]CST, Cell Signaling Technology; SYSY, Synaptic Systems; LT, Life Technologies.
[b]Rb, rabbit; Ms, mouse; Gt, goat; Ch, chicken; Rt, rat.
[c]M, monoclonal; P, polyclonal.

Mounting and Imaging.

According to the sample sizes, expanded hemispheres were mounted on a 60 mm-diameter petri dish, and shrunk hemispheres or other small samples were mounted on a slide glass. BLUE-TACK® Blue-Tack adhesive was applied on the petri dish or the slide glass, and samples were covered with a glass-bottom Willco dish. The space between the bottom material and the Willco dish around the sample was filled with either Shrinkage solution or DI water according to the sample immersion medium. Samples were stabilized for at least two hours before imaging. Samples were imaged with either Olympus FV1200MPE microscope system or Leica TCS SP8 microscope system. A 10×, 0.6 NA CLARITY-optimized objective (XLPLN10XSVMP; 8.0-mm walking distance) was used with the Olympus system to obtain wide-field images of shrunk samples. The images of expanded samples were obtained with a 10×, 0.3 NA water-immersion objective, a 20×, 0.95 NA water-immersion objective, and a 40×, 1.25 NA oil-immersion objective with the Olympus system, or a 10×, 0.3 NA water-immersion objective, a 25×, 0.95 NA water-immersion objective, and 63×, 1.30 NA glycerol-immersion objective with the Leica system. 405, 488, 555, and 635 nm lasers (Olympus) or a white-light laser (Leica) were used for the single-photon confocal laser scanning imaging. The images were visualized and analyzed with Fiji or IMARIS (Bitplane).

Large Tissue Staining.

1- and 2-mm-thick mouse brain coronal slices were prepared by general MAP protocol, and expanded. A 1-mm-thick slices was chopped to about 3 mm×3 mm×1 mm (dimensions before MAP). The sample was stained passively with ALEXA FLUOR™ Alexa Fluor 594-conjugated rabbit anti-GFP antibody (Life Technologies, A21312) for 3 days and ALEXA FLUOR™ Alexa Fluor 594-conjugated donkey anti-rabbit IgG antibody (Abcam, ab150072) for 3 days. 20 μL of antibody was used in 500 μL PBST, and was washed with 40 mL PBST for 1.5 days (three times in total) for each antibody. Stochastic electrotransport[33] was used to stain a 2-mm-thick slice with ALEXA FLUOR™ Alexa Fluor 647-conjugated rabbit anti-GFP antibody (Life Technologies, A31852) and ALEXA FLUOR™ Alexa Fluor 647-conjugated donkey anti-rabbit IgG antibody (Abcam, ab181347). For each antibody, a solution containing 20 μL of antibody in 4 mL of 0.6 M N-cyclohexyl-3-aminopropanesulfonic acid (CAPS), 0.2 M Tris, 100 mM NaCl, 20 mM SDS, 1% BSA (1:100 dilution) was first stochastic electrotransported with an electrophoresis buffer containing 0.3 M CAPS, 0.2 M Tris, 20 mM SDS, 30% sorbitol for 21 h. It was then stochastic electrotransported in a solution containing 4 mL of 0.3 M CAPS, 0.2 M Tris, 20 mM SDS, 30% sorbitol, 1% BSA, and 1% TRITON® Triton X-100 with an electrophoresis buffer containing 0.04 M Tris, 0.01 M phosphate, 30% sorbitol for 8 h. These two steps complete the stochastic electrotransport labeling. The stained sample was expanded in a solution containing 0.01% (wt/vol) heparin sodium procine mucosa (Sigma, SRE0027) and 1% TRITON® Triton X-100 in DI water, and then imaged.

Cell Distortion Analysis.

Before and after MAP processing tubulin images were first registered using a scaled-rotation transformation in ImageJ. Non-rigid invertible B-spline registration was performed with an 8×8 control point grid in bUnwarpJ. Vectors of different length were subjected to the resulting non-linear transformation, and the input-output difference norm was sorted based on the input vector length and then averaged by root-mean-square. For morphological image processing of nuclei, TOTO-1 images before and after MAP-processing were first registered using a scaled-rotation transformation in ImageJ. The registered images were segmented by thresholding and converted to circular particles with equivalent average radii calculated from the "Analyze Particles" function in ImageJ. Matched pairs of cells from the before and after images were randomly chosen, and the expansion ratio was calculated from the ratio of the connecting line segment lengths. The fraction in a nucleus was obtained by summing the intensity profile along the connecting line segment and averaging the sums from the before and after binary masks.

Tissue Distortion Analysis.

After anesthesia, mice were first washed transcardially with 2% AA in PBS followed by perfusion with 4% PFA and 30% AA in PBS. Thy1-eGFP-M mouse brains were harvested and incubated in 20 mL of the same fixative solution at 4° C. overnight and at 37° C. for 3 h. Brains were sectioned to 100-μm-thick coronal slices with a vibrating microtome. Slices were stained and imaged to obtain "before MAP" images, and then incubated in a solution containing 4% PFA, 30% AA, 0.1% BA, 10% SA, and 0.1% V50 in PBS at RT for 8 h. Hydrogel-tissue hybridization was performed in situ by incubating the tissues with nitrogen gas at 45° C. for 2 h. Hydrogel-embedded tissues were incubated in denaturation solution at 37° C. for 1 h and 95° C. for 0.5-1 h. Samples were then stained with the same markers and imaged to obtain "after MAP" images.

To quantify distortion errors, regions approximately 3 mm×2.5 mm in size that included cortex and hippocampus were stained with DYLIGHT™ DyLight 594-conjugated lectin (Vector Laboratories, DL-1177) before (8 µL in 200 µL PBST for up to 8 samples) and after (2 µL in 200 µL PBST for each sample) MAP processing. Samples were incubated in RI matching solution after staining and mounted and imaged before MAP processing. Five samples were repeated for incubation, mounting and imaging to measure mounting errors. After MAP processing, six samples were stained, expanded in DI water, and imaged. Keypoints of the vasculature in volumetric images were detected and matched between two image sets with a MATLAB code implementing the 3D Harris Corner Detector and 3D SIFT algorithm as described previously[13]. Using custom-built graphical user interface software developed with DELPHI® Delphi XE4 (Embarcadero Technologies), redundant keypoints closely located to each other and keypoints at tissue margins were removed. Tissue sizes were estimated by the area defined by a convex hull encompassing all keypoints, and the expansion ratio was calculated as the ratio between two squared roots of the areas. The correspondence information was used to generate a regularly spaced deformation mesh using a 3D thin plate spline code written by Yang, Foong, and Ong and available at Mathworks website, matlabcentral, fileexchange, search for thin plate spline warping function. Lengths between each pair of grid points were calculated in both pre-MAP and post-MAP images, considering the expansion ratio. The difference between the two lengths was measured as a distortion error. After averaging the squared errors for each measurement length, the square root of the averages was collected from the samples to obtain statistical values of error.

Neurofilament Tracing.

Tracing of individual neurons was performed using either Fiji or Imaris software. For the manual tracing of a long TH fiber, a representative fiber was chosen during confocal imaging acquisition, and traced with moving the motorized stage and adjusting z-level. During the tracing, any ambiguous crossing-overs were resolved with obtaining high-magnification subvolume images. After tile-scanning, the target fiber was re-identified from the image volume using Fiji, and marked to be displayed in a two-dimensional plane. For the semi-automatic tracing of fibers in a dense region, the entire 800 µm×800 µm×150 µm (expanded) dataset was loaded along with a filament tool into a 'Surpass' instance using Imaris software. An autopath calculation was performed using a single starting point (data not shown). The fiber endpoint was designated by selecting the portion of the fiber exiting the imaged volume. The fiber representation was changed to a cone representation to visualize the filament diameter as well as the tracing path. The tracing fidelity was confirmed by inspection. In order to trace multiple fibers a dense region, the full dataset was cropped to the region indicated in FIG. 3D using the '3D crop' tool, and similar autopath calculations were performed for each fiber.

Synaptic and Fiber Intensity Profiles.

Figure 2A:
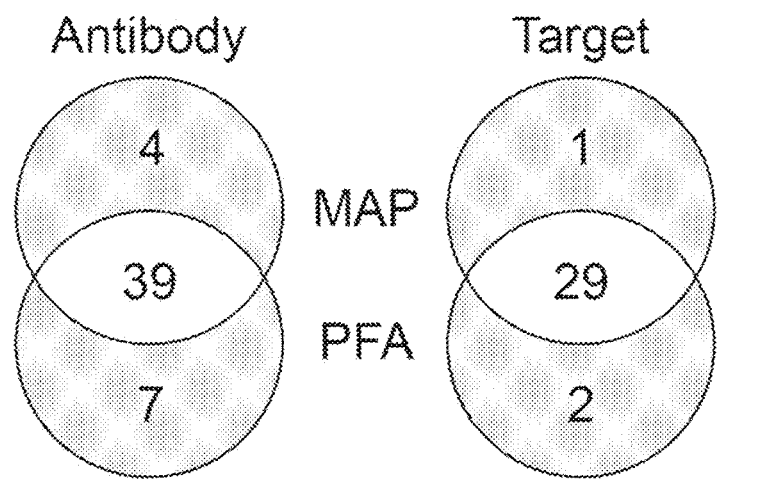
FIGS. 2A-2M: MAP preserves the 3D proteome library and subcellular details of an intact tissue and enables its multiplexed super-resolution imaging.
Figure 2B:
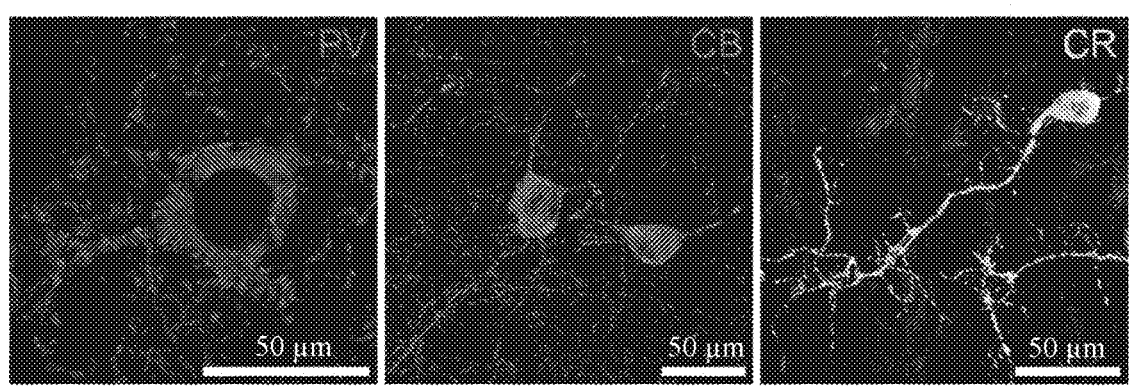
Figure 2C:
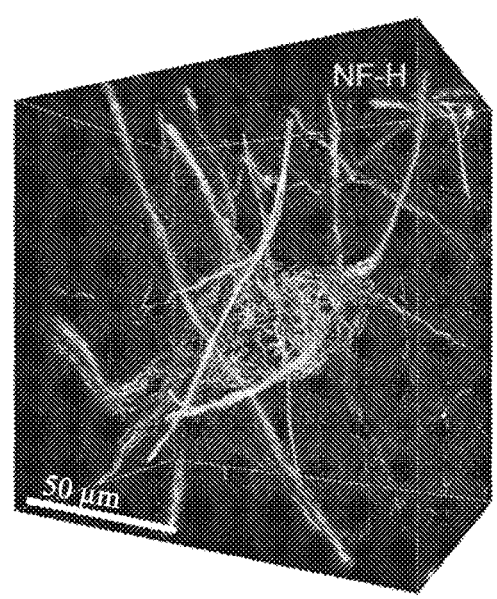
Figure 2D:
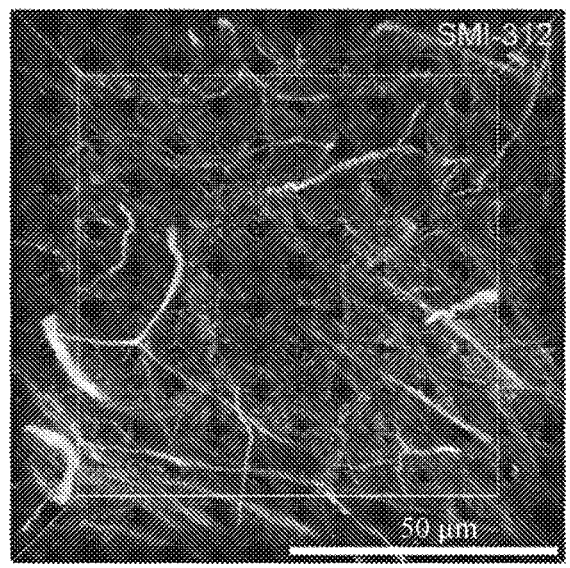
Figure 2E:
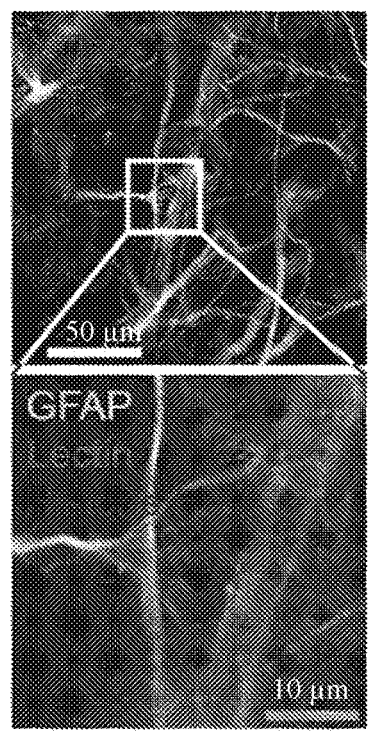
Figure 2F:
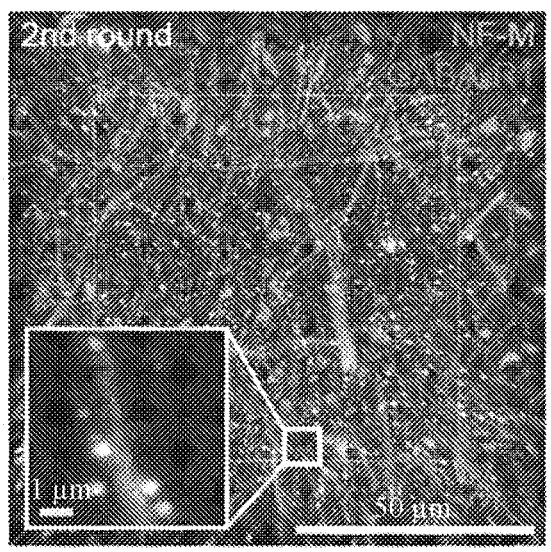
Figure 2G:
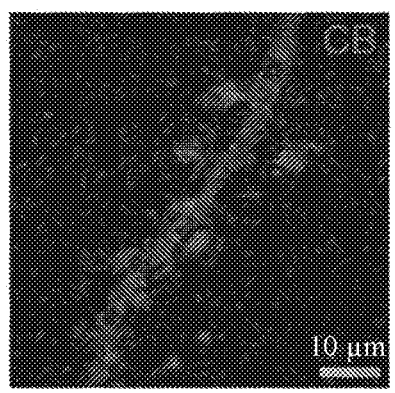
Figure 2H:
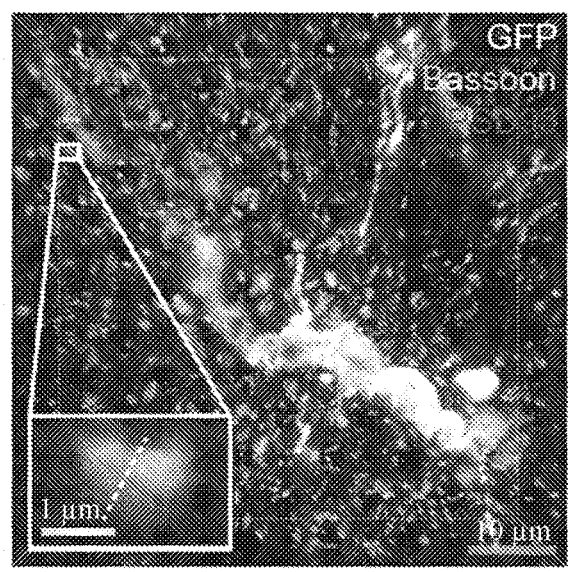
Figure 2I:
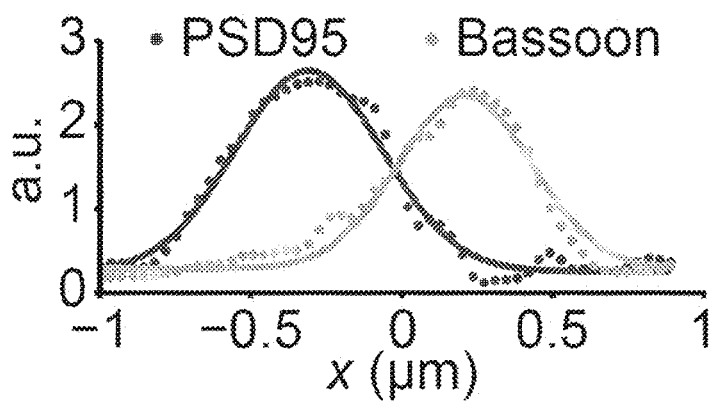
Figure 3A:
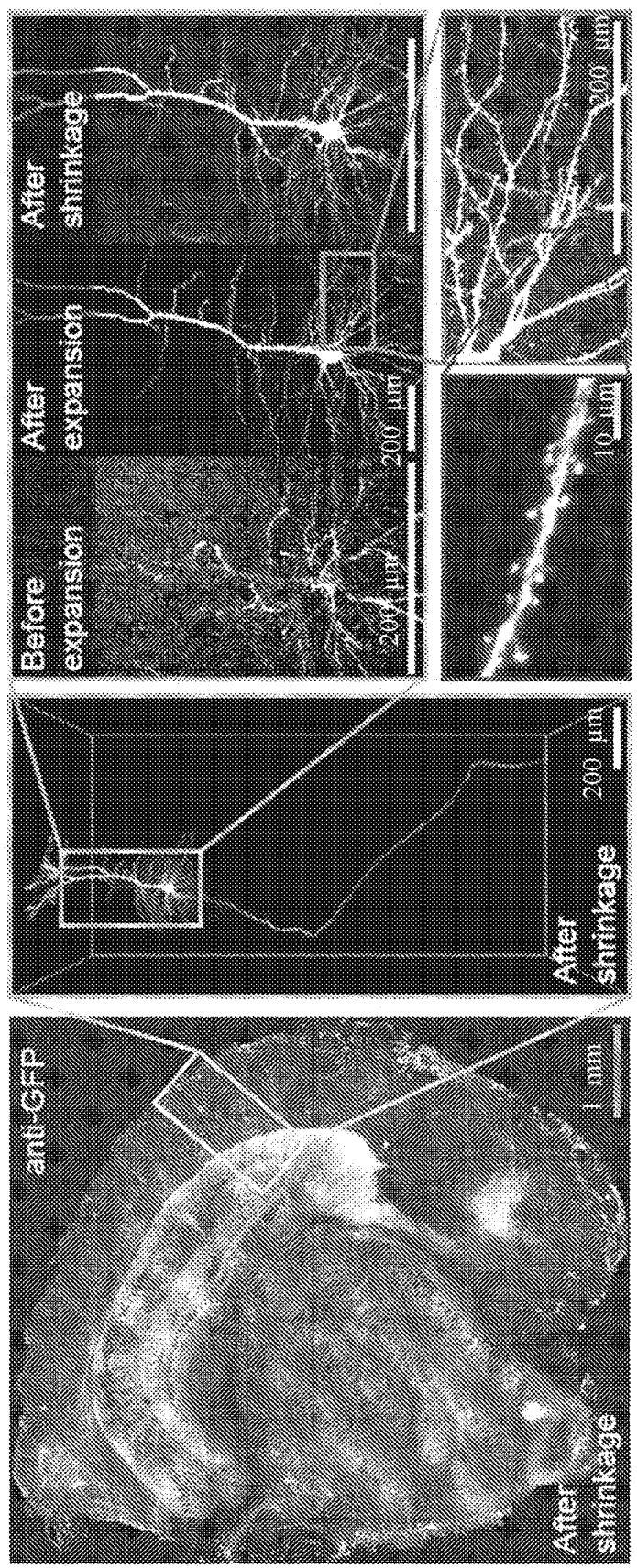
FIGS. 3A-3D: MAP preserves inter-cellular connectivity and enables its reconstruction at single fiber resolution.
Figure 3B:
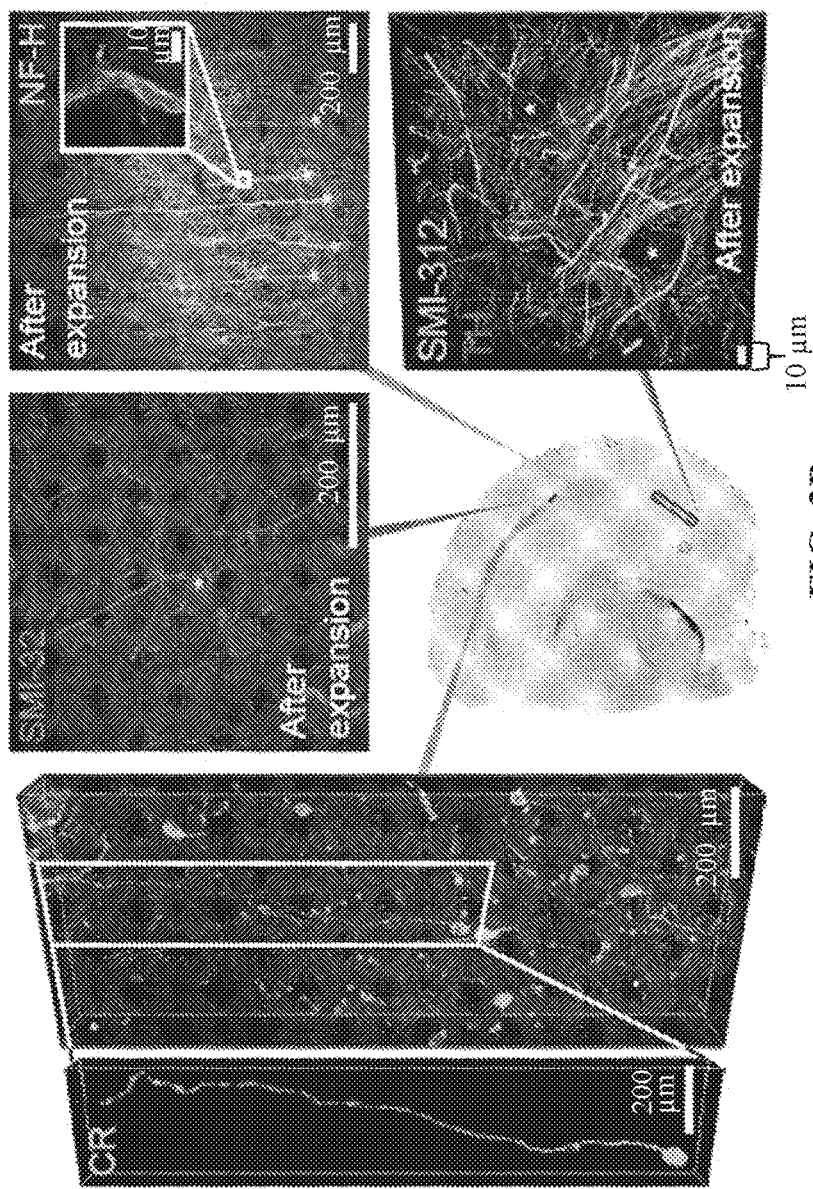
Figure 3C:
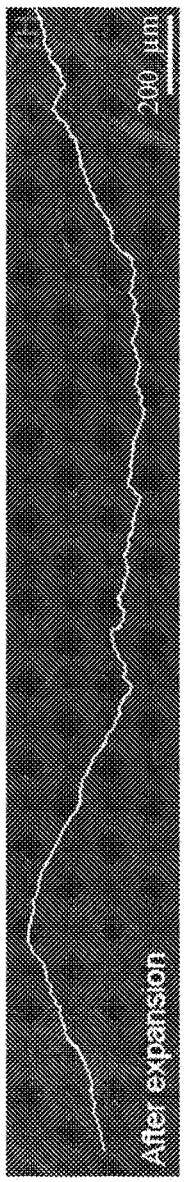
Figure 3D:
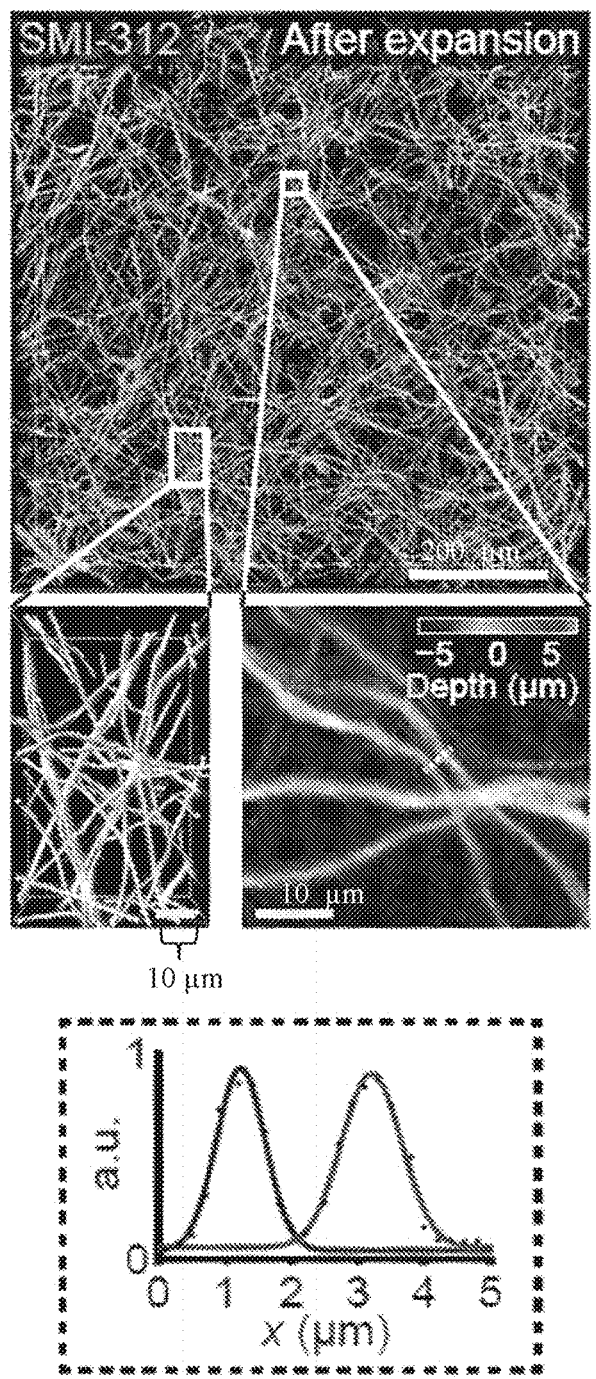

The ROIs indicated in FIGS. 2G and 3D were imported into Fiji. Three parallel, centered lines were drawn perpendicular to the synaptic junction or near the fiber crossing and intensity profiles were obtained. The three intensity profiles were averaged and two Gaussian distributions were fit to the distinct peaks by simultaneous minimization of the sum of squared residuals. Synaptic densities for bassoon and VGluT2 were calculated from three non-overlapping xy-images (235 µm×235 µm) of expanded samples. The images were segmented by thresholding, and individual synaptic structures for each channel were counted using the "Analyze Particles" function in Fiji. The synaptic densities were calculated based on the frame area, and the standard deviation was calculated from the three replicates.

Results

Biological systems such as the brain consist of thousands of distinct cell types forming hundreds of interconnected functional areas[1-5]. Understanding how these diverse cells interact to generate systems-level responses is essential for many fields of biology. The study of such complex interactions may benefit from tools that enable holistic reconstruction of cellular connectivity, molecular details, and fine subcellular architectures of individual cells and their surrounding tissue environment.

Antibody-based proteomic imaging strategies have the potential to provide such multi-scale information[6-10]. Super-resolution imaging of immunolabeled thin tissue sections has been successfully used to reconstruct minute subcellular structures (e.g., neuronal processes and chemical synapses)[11]. Emerging intact tissue clearing techniques preserve the continuity of long-range projects and may allow reconstruction of brain-wide inter-areal connectivityl[2,13]. Pioneering multiplexed proteomic imaging tools can provide rich molecular details of individual neurons and may allow reconstruction of their surrounding tissue environment[14-18]. Combined extraction of this multi-scale information might offer new opportunities to define fundamental cell types and study their system-wide complex interactions. Yet, such integrated study remains an unmet goal in biology.

To address this challenge, a goal was set of developing a robust method that enables magnified proteomic imaging of intact biological systems for combined extraction of subcellular architectures, connectivity, and molecular details from a single tissue. To achieve this, the MAP (Magnified Analysis of Proteome) technique was developed, which preserves both the three-dimensional (3D) proteomic library and organ-wide cellular connectivity within an intact tissue-hydrogel hybrid while making it size-adjustable up to 4- to 5-fold linearly for multi-resolution imaging (FIG. 1).

The key to this method is to prevent intra- and inter-protein crosslinking during the hydrogel-tissue hybridization step[19] and then to dissociate and denature proteins to allow natural expansion of the hybrid (FIG. 1A). It was hypothesized that high concentrations of acrylamide (AA) monomers might effectively prevent protein crosslinking by quenching reactive methylols formed by the protein-formaldehyde reaction. If the AA monomer concentration is low, the reactive methylols would react with amide groups within the same protein or adjacent proteins to form methylene bridges (FIG. 1A, left column)[20]. Such intra- and inter-protein crosslinking would prevent dissociation of protein aggregates and their complete denaturation[21], which would limit subsequent tissue expansion. On the other hand, if the AA concentration is high (FIG. 1A, right column), methylols might preferentially react with excess AA monomers, effectively preventing intra- and inter-protein crosslinking while tethering the proteins to an expandable hydrogel mesh.

Denaturing and linearizing such non-crosslinked proteins may allow natural expansion of the hydrogel-tissue hybrid while preserving the proteomic library at its physiological location.

Figures 1, 1A, 2:
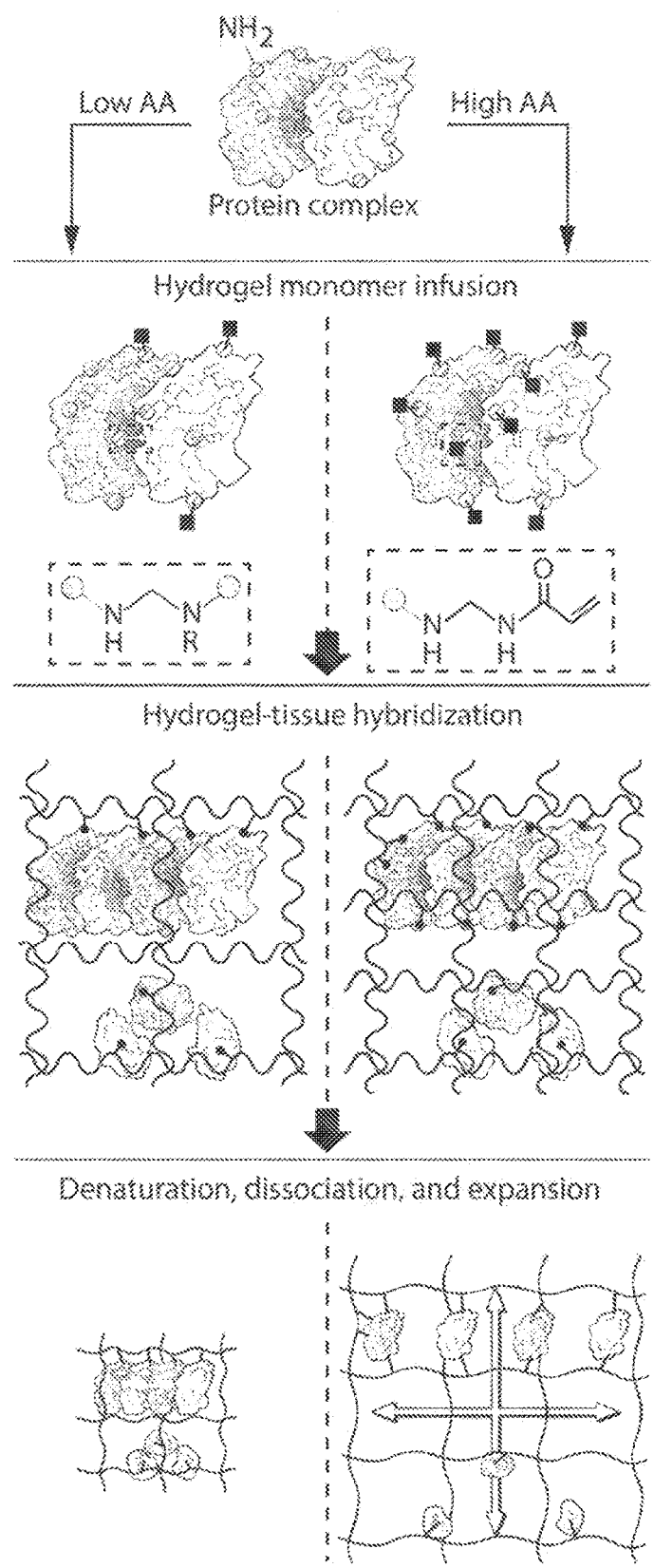
Figure 1B:
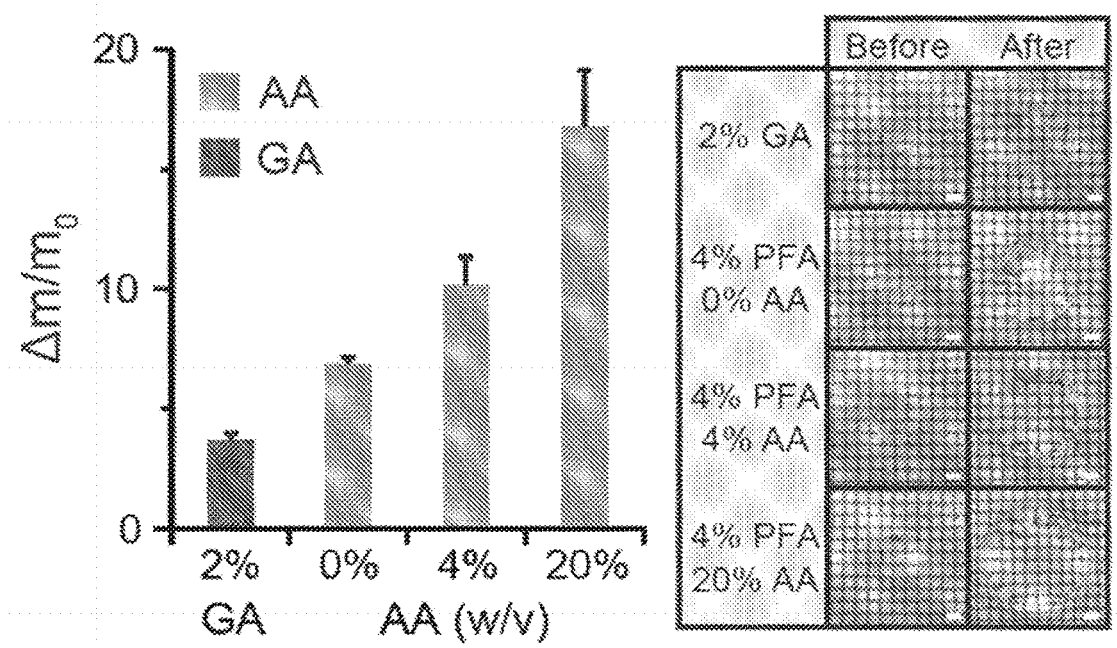
Figure 1C:
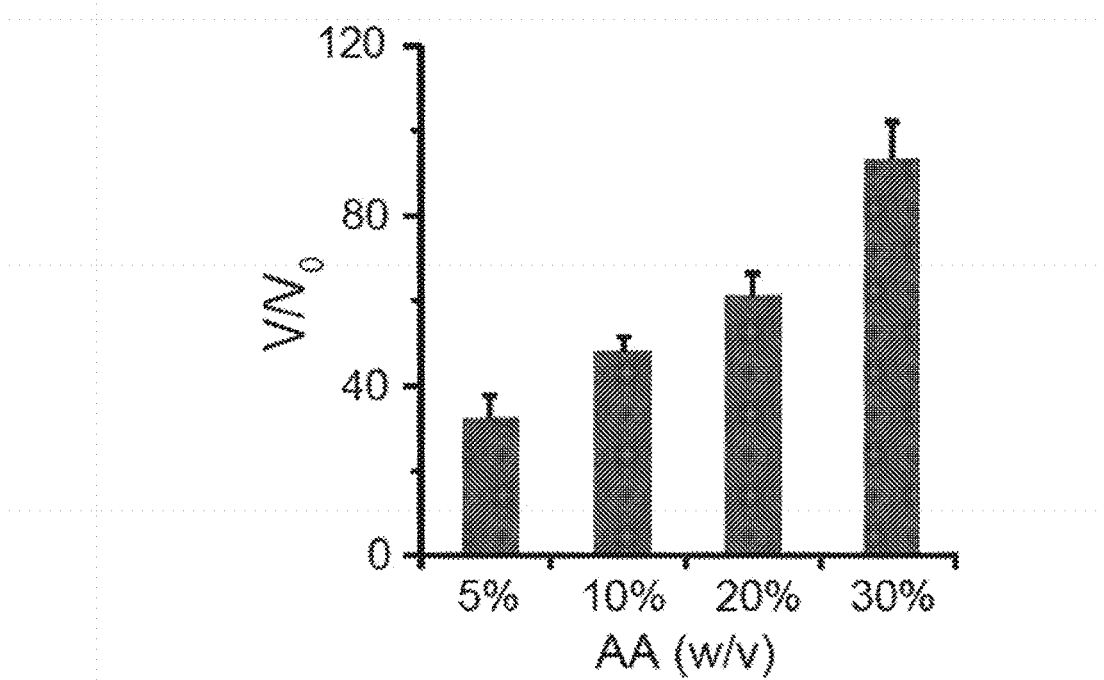
Figure 1D:
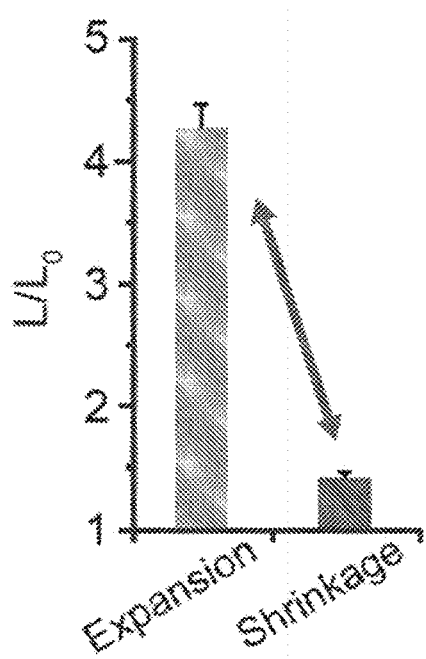
Figure 1E:
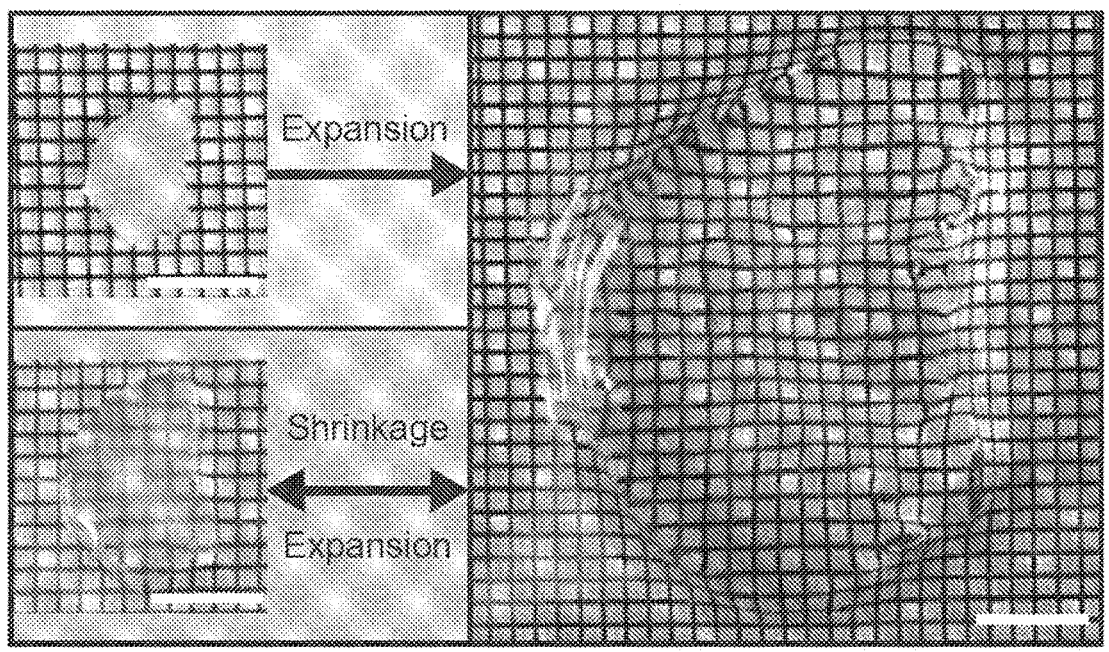
Figure 1F:
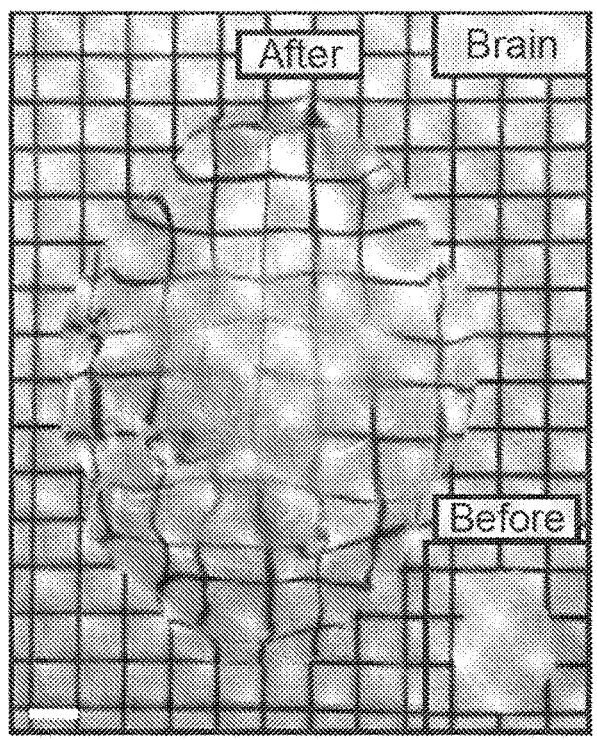
Figure 1G:
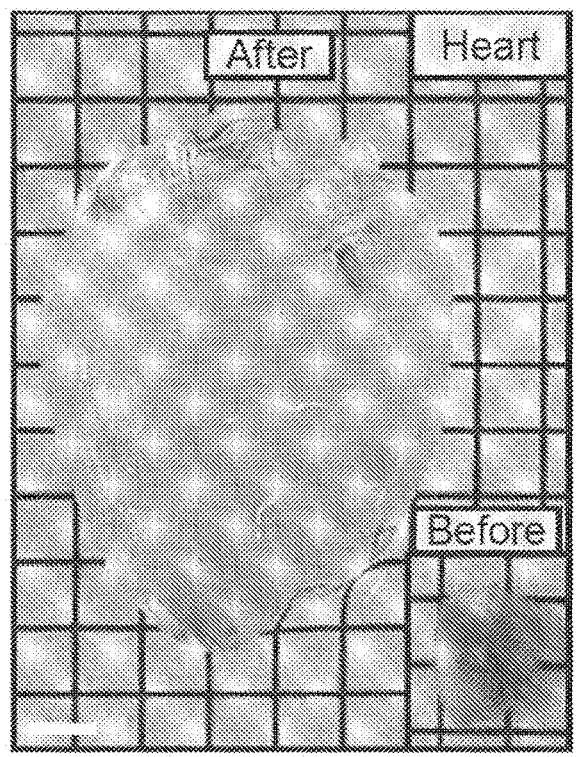
Figure 1H:
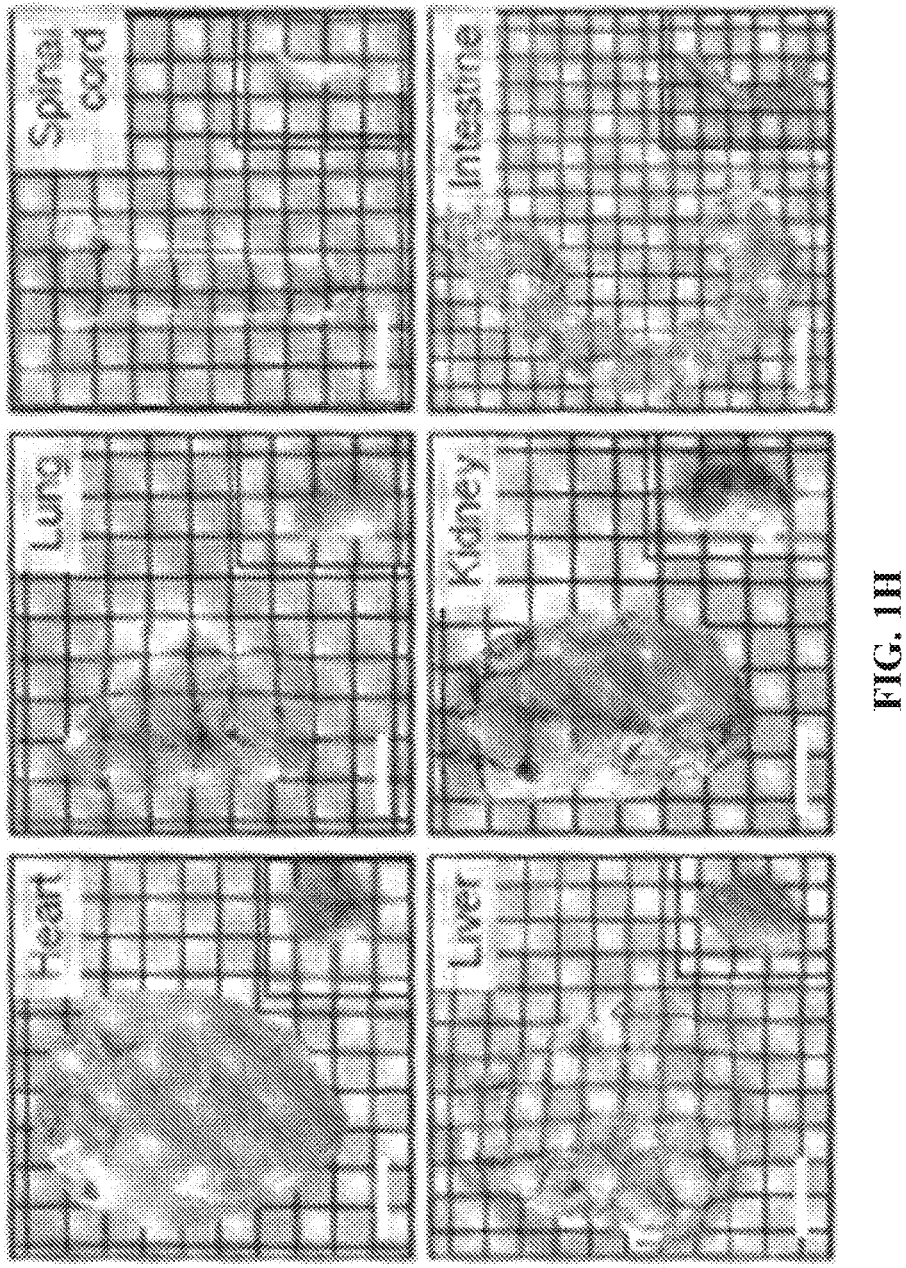
Figure 1I:
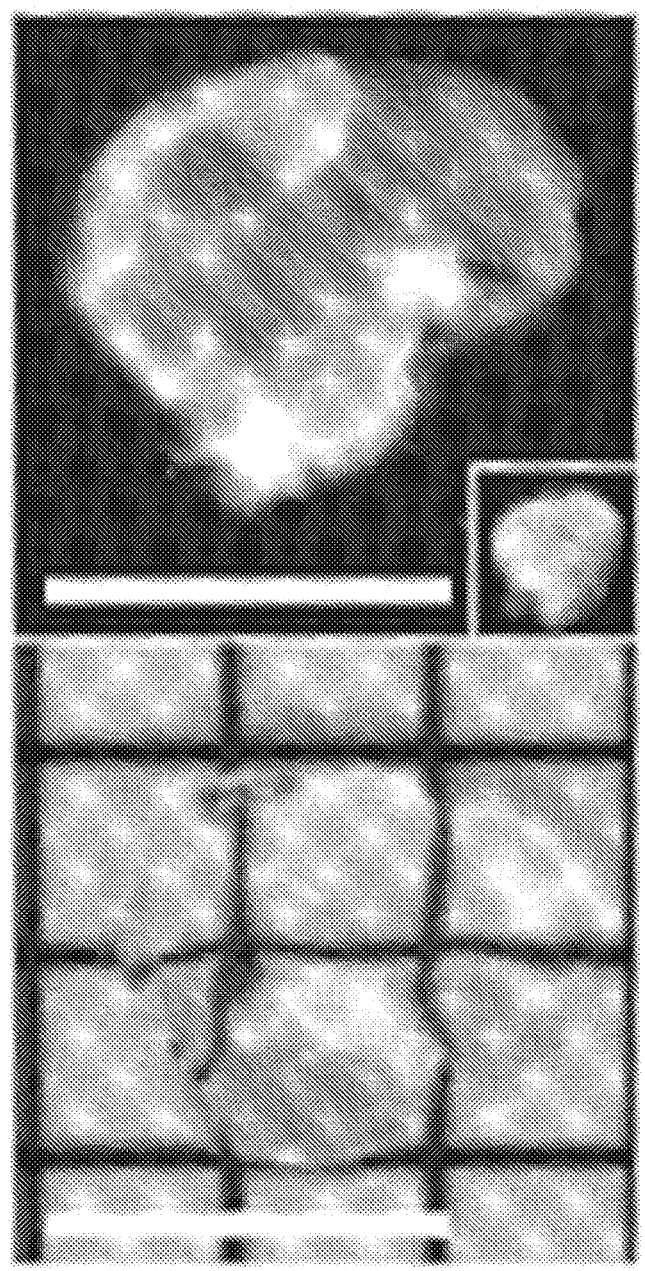

To test this hypothesis, hydrogels were made using bovine serum albumin (BSA) that were formaldehyde-fixed in different concentrations (0-20%) of AA and then incubated the gels in 80° C. detergent solution to disrupt the secondary and tertiary structure of BSA (FIG. 1B). As expected, gels made with BSA that were fixed in higher concentrations of AA showed higher degrees of expansion (FIG. 1B). The same trend was observed in intact tissues (FIG. 1C). Using this three-step approach (FIG. 1A), it was possible to achieve 4- to 5-fold linear expansion of a whole mouse brain within only 7 days while preserving its denatured protein library (FIG. 1F). The tissue expansion is a reversible and tunable process. It was possible to reversibly adjust the tissue size using buffers with different salt concentrations and osmolalities (FIGS. 1D-1E and 3A). In addition, the versatility of the approach was demonstrated by processing and expanding several other organs, including heart, lung, spinal cord, liver, intestine, and kidney (FIG. 1G and data not shown).

It was next asked if MAP secures multiscale structural information and enables superresolution imaging with diffraction-limited microscopes. To estimate the amount of distortion incurred from expansion, gel-embedded cultured cells were imaged before and after MAP processing. At the subcellular scale, MAP expansion improved visualization of microtubules and allowed imaging of fine structures (data not shown). The estimated distortion error (root-mean-square error, RMSE) was less than 3% of measured length at both the subcellular scale and the multicellular scale (data not shown). The degree of gel expansion was not a function of cell density, as indicated by the consistent local expansion within differently populated cell clusters (data not shown).

To test if MAP preserves multiscale tissue architectures, a 100-µm-thick mouse brain block labeled with lectin was imaged before and after MAP. The distortion analysis showed less than 4% error, which was at most a two-fold increase, compared to the inevitable distortion from sample mounting for imaging (data not shown). Both the intra-capillary space with low protein concentration and the extra-capillary space with high protein concentration showed similar degrees of expansion, suggesting that the effect of protein concentration and cell density on gel expansion is minimal. Diffraction-limited microscopy revealed fine 3D details of immunolabeled cells such as cytoskeletal filament structures and better-resolved axonal fibers after the MAP process. These results together indicate that MAP preserves multiscale structural information of biological samples and enable superresolution imaging with diffraction-limited microscopes.

It was next asked if the proteome library is well preserved within the magnified tissue-gel hybrid and if it can be visualized using commercially available antibodies. Antibody targets were selected from a wide range of antigens (e.g., membrane proteins, cytoplasmic proteins, nuclear proteins, neurofilament [NF] proteins, and synaptic proteins) in order to better represent the overall proteomic landscape (FIG. 2, Table 1, and data not shown). It was found that 43 of 50 antibodies were compatible with the processed samples, and 30 of 32 target proteins were successfully visualized (FIG. 2, Table 1, and data not shown), indicating that loss of epitopes by protein denaturation is minimal. This might be because synthetic peptides or denatured protein fragments are commonly used for conventional antibody production[22]. However, some antibodies (e.g., parvalbumin [PV] and calbindin [CB]) showed negative staining when different antibodies targeting the same endogenous protein showed strong signal (FIG. 2B and Table 1). This result demonstrates that the tissue proteome is well secured in MAP with minimal loss of specific epitopes and the library can be effectively probed using off-the-shelf antibodies without any modification.

We investigated whether MAP preserves minute structures and enables repeated interrogation of their molecular architecture within the same tissue. Antibodies targeting filament proteins successfully visualized fine details of the cytoskeletal networks of various cell types (FIG. 2C-E). No connectivity loss was observed in the magnified tissues, indicating that filament continuities were well preserved. Labeling of glial fibrillary acidic protein (GFAP) visualized the fine foot process structures surrounding blood vessels (FIG. 2E)[23,24]. NF medium subunit (NF-M) visualized both processes and spine-associated structures, a subset of which co-localized with the C-terminal domain of the $GABA_B$ receptor subunit-1 ($GABA_BR1$) (FIG. 2F). Labeling of calcium-binding proteins (PV, CB, and calretinin [CR]) robustly visualizes morphological details of positive cells (FIG. 2B). A small subset of CB-positive fibers showed expression of CB in their dendritic spines (FIG. 2G).

Figure 2J:
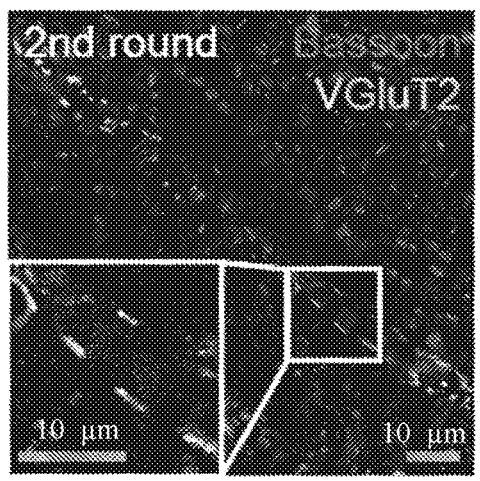
Figure 2K:
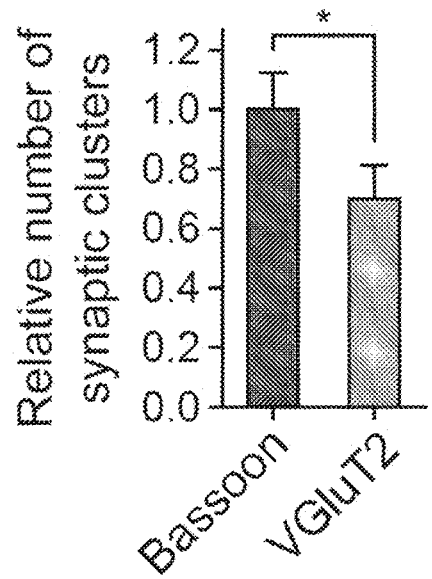
Figure 2L:
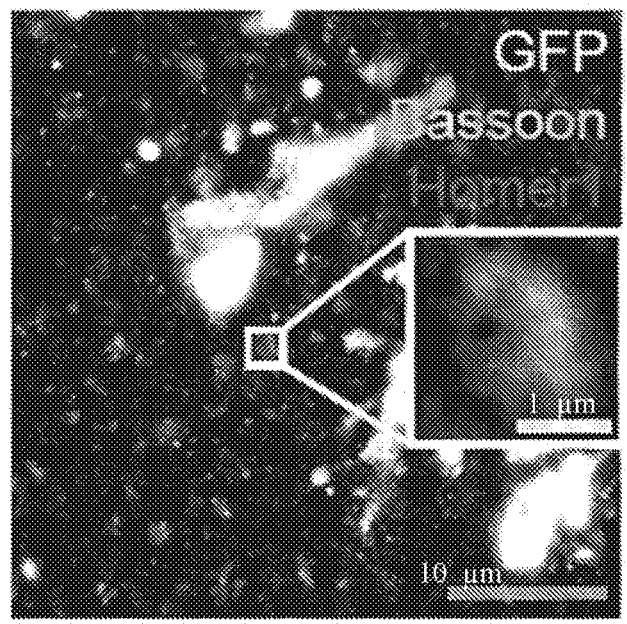
Figure 2M:
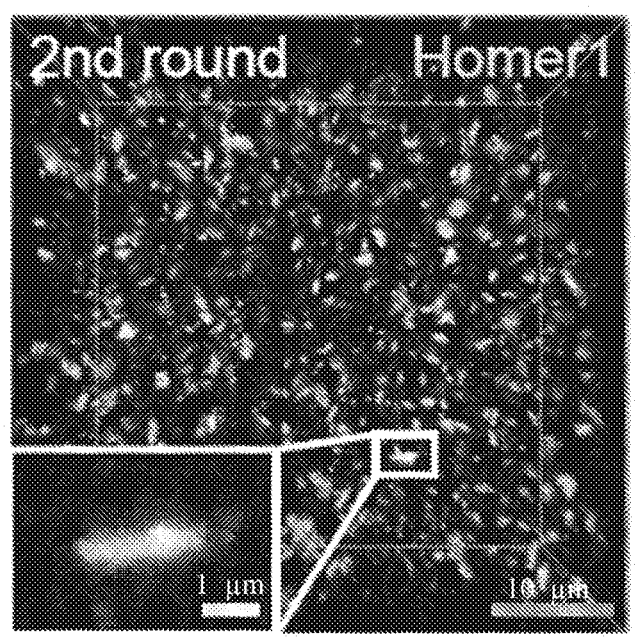

Many synaptic proteins markers could be assessed using MAP as shown in FIGS. 2H, 2J, 2L, 2M and Table 1). Staining of synaptic proteins clearly visualized distinct and well separated elliptical disk-shape clusters of pre- and post-synaptic proteins (FIG. 2H, 2L), enabling their quantitative analysis (FIG. 2K). In addition, MAP allows repeated staining and imaging of the magnified 3D proteome within a single tissue. It was possible to elute imaged probes and relabel the same tissue using another set of antibodies to visualize new targets (FIGS. 2F, 2J, 2M and data not shown). These results demonstrate that MAP preserves fine subcellular structures and enables their multiplexed interrogation using rich antibody library and diffraction limited microscopy.

Another key advantage of the MAP technology is that it enables highly multiplexed labeling and imaging of the magnified 3D proteome within a single tissue. Seven rounds of immunostaining of a MAP-processed 100-µm-thick mouse brain tissue were successfully performed with no obvious signs of tissue damage (data not shown). Outstanding mechanical stability of the MAP-processed sample enabled repeated manual handling of the tissue with tools that are widely used in biology labs. The images after destaining of the imaged anti-GFP antibody (first round) and after solely adding secondary antibodies targeting the eluted anti-GFP antibody (second round) showed little signal, suggesting that the destaining process effectively eliminates antibodies. For the following five rounds of labeling, anti-GFP continued to be used as a landmark in addition to two other antibodies for each round. The consistent GFP signals show that the same antigen can be repeatedly labeled without loss of antigenicity. Successful visualization of ten other targets demonstrates that MAP facilitates exploring diverse proteins, structures, and cell types within a single tissue.

The potential utility of MAP for mapping brain-wide neural connectivity at single-cell resolution was next explored. Reconstructing brain projectome, all the areal projections within a single brain, remains an important but unattainable goal in neuroscience[25]. Individual fibers often cannot be resolved using diffraction-limited imaging, prohibiting accurate projection tracing. Super-resolution fluorescence imaging techniques (e.g., STORM, STED, and PALM) can significantly increase the accuracy of reconstruction but are currently not scalable to organ-sized samples[9,26,27]. Expansion microscopy (ExM) has recently enabled super-resolution imaging of thin tissue sections using diffraction-limited microscopes[28]. However, neural connectivity is lost in this method owing to tissue sectioning, which is currently required for the delivery of ammonium persulfate, a highly unstable initiator. Moreover, the protease digestion step causes loss of the proteome library. Therefore, only a limited number of protein targets can be labeled to visualize neural processes in this method.

If MAP could preserve brain-wide neural connectivity within a magnified intact brain along with its 3D proteome, it might enable visualization of the areal connectivity of the neuronal subpopulations using highly specific antibodies. The enhanced spatial resolution and selective labeling of subpopulations offered by MAP may allow accurate reconstruction of the neurons and their long-range projections. In addition, highly multiplexed proteomic imaging may enable reconstruction of many different cell-types with integrated molecular and fine morphological details within a single tissue.

To explore this possibility, we asked if the continuity of neural processes is preserved within a magnified sample. A 1-mm-thick Thy1-eGFP mouse brain coronal block was expanded by 4-fold linearly and then imaged GFP-labeled neurons and their projections[29]. As shown in FIG. 3A, the continuity of the GFP-expressing projections spanning a large tissue volume was well preserved. The fine morphological details (e.g., dendritic spines) could also be observed from the same GFP-expressing neurons (FIG. 3A). This result demonstrates that MAP preserves both long-range neural connectivity and subcellular details and enables interrogation of both properties within a single sample.

Building on this result, we investigated whether the 3D proteome library can be used for visualizing diverse neural subpopulations and their areal connectivity. Antibodies targeting various cytoplasmic proteins including NF proteins (e.g., NF-M and NF-H), calcium-binding proteins, and metabolic enzymes (e.g., tyrosine hydroxylase [TH]) were tested (FIG. 3B). TH staining robustly visualized both fine processes and long-range projections of TH-positive cells (FIGS. 3B-3C). The highly selective labeling, preservation of fiber continuity, and enhanced resolution offered by MAP made it possible to reliably trace individual TH-positive processes within the large imaging volume (3.5 mm×2.3 mm×0.4 mm after expansion) (FIG. 3C). The enhanced resolution was particularly useful in tracing densely packed fibers visualized by NF protein markers (FIG. 3D). Other antibodies tested also robustly visualized areal projections of the important cell types (FIG. 3B).

To test if MAP enables more accurate tracing of densely packed fibers, NF-stained samples were imaged before and after MAP processing using a high NA (0.95) water-immersion objective. Two individuals not involved in imaging acquisition traced fibers within the sample volume (data not shown). When the concordance between the two tracing results was compared, the discordant rate was significantly lower after MAP (data not shown) even though MAP enabled the tracers to detect more fibers (total numbers of traced fibers were 160 before MAP and 214 after MAP). This result demonstrates that MAP indeed enables more accurate reconstruction of immunolabeled neural fibers.

Reconstruction of individual neurons requires labeling and imaging of thick brain tissues because nerve fibers can extend across a large volume. To test if MAP is applicable to large-scale brain tissues, a 1-mm-thick mouse brain block (5-mm-thick after expansion) was expanded and passively stained with anti-GFP antibody. The sample was then imaged using both a high NA (0.95), short WD (2 mm) water-immersion objective and a low NA (0.6), long WD (8 mm) CLARITY objective. Both objectives showed fine dendritic spines of GFP-expressing neurons throughout the entire volume. Imaging of the sample did not require depth-dependent modulation of the laser power, indicating that staining was uniform and that signal attenuation by light scattering was negligible. MAP is also compatible with stochastic electrotransport[33], a method that enables rapid tissue labeling. Using stochastic electrotransport, it was possible to label an 8-mm-thick expanded tissue uniformly within only two days. The sample was highly transparent. The 8-mm-thick sample was successfully imaged with the same laser power up to the WD of the objective.

As a step toward organ-scale reconstruction of cells and their surrounding environment, and to advance the study of complex system-level interactions, a robust and scalable method was developed that enables preservation, reversible magnification, and imaging of a 3D proteome library within an intact tissue. The proteome is an ideal substrate for such reconstruction owing to proteins' unmatched diversity, functional roles, and distinct subcellular localization at single-molecule precision. We discovered that the 3D proteome library of a whole organ can be preserved and magnified by preventing intra- and inter-protein crosslinking, denaturing the proteins, and allowing natural expansion of hydrogel-tissue hybrids. The magnified hybrids secure both fine subcellular architectures and organ-scale cellular connectivity. These multi-scale properties can be directly imaged by using antibodies to label the structures' constituent proteins and peptides. An existing large antibody library (close to 100,000 antibodies, corresponding to >70% of the protein-coding genes in humans, currently available)[10], once validated, can be used without any modification. This technique is easy to implement, and it does not require any special equipment or chemicals.

The reversible modulation of the physical sample size that is attained with MAP enables multi-scale proteomic imaging of a single tissue to capture both system-scale properties and the finest local details in a practical way. For example, following sample shrinkage, global projection patterns of labeled neurons may be imaged using high-speed microscopy techniques and long working distance objectives (e.g., 25×, 1.0 NA, 8 mm WD objective, currently available)[12,30]. After imaging, the same tissue can be expanded for super-resolution imaging of regions of interest. The expanded tissue may need to be sliced prior to imaging to meet the objective's working distance limit. A microscope with a built-in vibrating-blade microtome could also be used for whole-mount imaging to avoid loss of connectivity information[31]. This approach can allow the imaging time and the costs associated with data storage and handling of expanded samples to be drastically reduced.

MAP enables repeated interrogation of a magnified 3D proteome library. This is possible because the preserved epitopes, which have already reached complete denaturation by harsh treatment (80-95° C., 200 mM SDS) for expansion, should not undergo any further modification during the milder antibody elution step (70° C., 200 mM SDS). This unique advantage of MAP may allow combined extraction of rich molecular details, minute subcellular architectures, and cellular connectivity from diverse cell types within a single tissue. Together with its simplicity and broad applicability, MAP may complement existing powerful methods and enable new approaches in the study of complex biological systems.

MAP has the potential to enable scalable superresolution imaging of large-scale samples. Unlike other methods, thick tissues can be labeled on a practical time scale because antibody-labeling occurs after complete lipid removal and tissue permeabilization. The great transparency of the MAP-processed samples allows high-resolution imaging of the physically expanded tissue with minimal loss of resolution. Currently, 1.0 NA, 2.5-mm WD water immersion objectives are best suited for MAP. Although the 1.0 NA, 8-mm WD CLARITY objective has the longest WD, it does not provide high quality images because it is optimized for immersion media with a high refractive index (RI). Further development of high NA, long WD water objectives or the development of high RI immersion media that are compatible with MAP would extend the utility of MAP. Another challenge in the MAP approach is the dilution of fluorescent signals that accompanies physical volumetric expansion. Four-fold linear expansion decreases signal density by 64-fold. Therefore, significantly higher laser power is required, which in turn causes photobleaching. Future studies will need to explore the compatibility of signal amplification techniques with MAP.

The unique advantages of MAP may allow combined extraction of rich molecular details, minute subcellular architectures, and cellular connectivity from diverse cell types within a single tissue. Together with its simplicity and broad applicability, MAP may complement existing powerful methods and enable new approaches in the study of complex biological systems.

Example 2: Tissue/Cell-Hydrogel Hybrid without or Reduced Chemical Linking-Materials and Methods. Hybridization without Chemical Linking A sample of tissue or cultured cells was prepared either by use of a previously fixed and stored sample, or by perfusing and fixing an animal with PFA, or by fixing cultured cells with PFA. To obtain fixed mouse brain, wild-type or Thy1-eGFP-M mice were perfused transcardially with ice-cold PBS solution, followed by a solution of 4% PFA in PBS. After extracting the brain, the brain was fixed in 4% PFA in PBS solution overnight at 4° C. and incubated at 37° C. for 3 h. The brain was washed with PBS containing 0.02% sodium azide at room temperature (RT) overnight with one solution change. The brain was cut in some instances to obtain small or thin samples where required. Remaining reactive groups such as methylol groups in the sample were quenched by incubating in a solution containing 1% wt/vol glycine and 1% wt/vol acetamide at pH 9.0 overnight at RT, and washed with PBS containing 0.02% sodium azide at RT overnight with one solution change.

The fixed sample was then incubated in a hydrogel subunit solution containing 30% AA, 10% SA, 0.1% BA, 0.02% V-50 and PBS. The incubation times for whole brain samples, hemisphere samples, 2-mm-thick samples, 1-mm-thick samples and 100¬-160-µm-thick samples were 1 week, 5 days, 3 days, 2 days and 1 day, respectively. The sample was embedded at 45° C. for 2 h, and cleared either passively at 50° C. or using a stochastic electrotransport method at 37° C. For passive clearing, whole brain and hemisphere samples were cleared for 1 week, 2-mm- and 1-mm-thick samples were cleared for 1-3 days, and 100-160-µm-thick samples were cleared for 1-6 h until the sample is transparent. For stochastic electrotransport clearing, whole brain and hemisphere samples were cleared for 2-3 days. Cleared samples were washed with PBS containing 0.02% sodium azide or expanded in DI water until the detergent was removed or the expansion was complete, depending on the tissue size.

Results

Figure 4A:
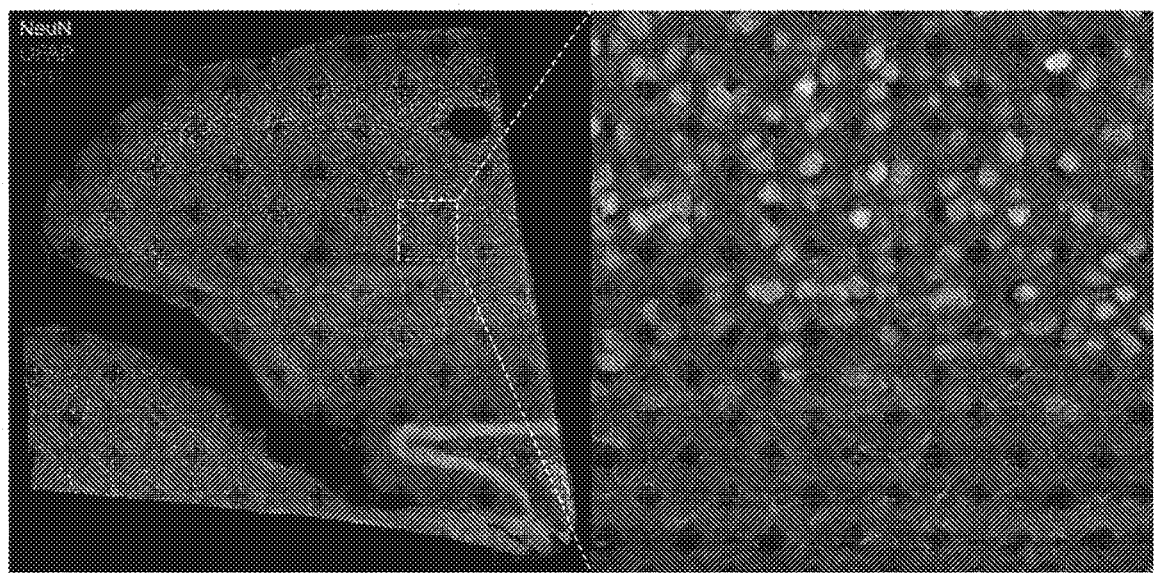
FIGS. 4A and 4B: Immunostaining of mouse tissue hybridized into a hydrogel without chemical linking of biomolecules of the tissue with the hydrogel.
Figure 4B:
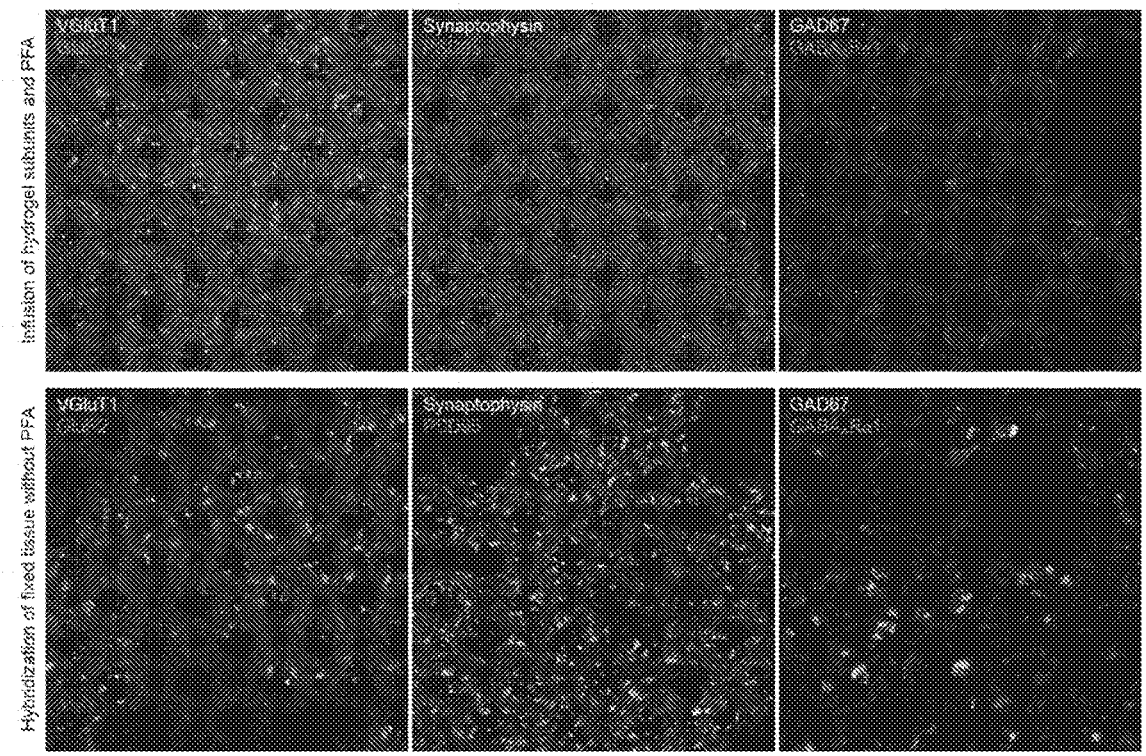

A fixed mouse brain was embedded into a hydrogel comprising 30% acrylamide, 10% sodium acrylate and 0.1% bis-acrylamide without paraformaldehyde. The biomolecules inside the tissue were not chemically linked to the hydrogel during this process. However, nevertheless, the tissue-hydrogel hybrid was capable of expansion and showed well-preserved proteins structure (and thus tissue integrity) as evidenced by staining with antibodies (FIG. 4A). Also, with less modified polypeptides this type of tissue-hydrogel hybrid (i.e., MAP2) showed more specific labeling of diverse synaptic proteins with improved signal (FIG. 4B, bottom panels), compared to chemically hybridized tissue-hydrogel hybrid (i.e., MAP1; FIG. 4B, top panels).

Example 3: Tissue/Cell-Hydrogel Hybrid in a Hydrogel with No Acrylate

Figure 5:
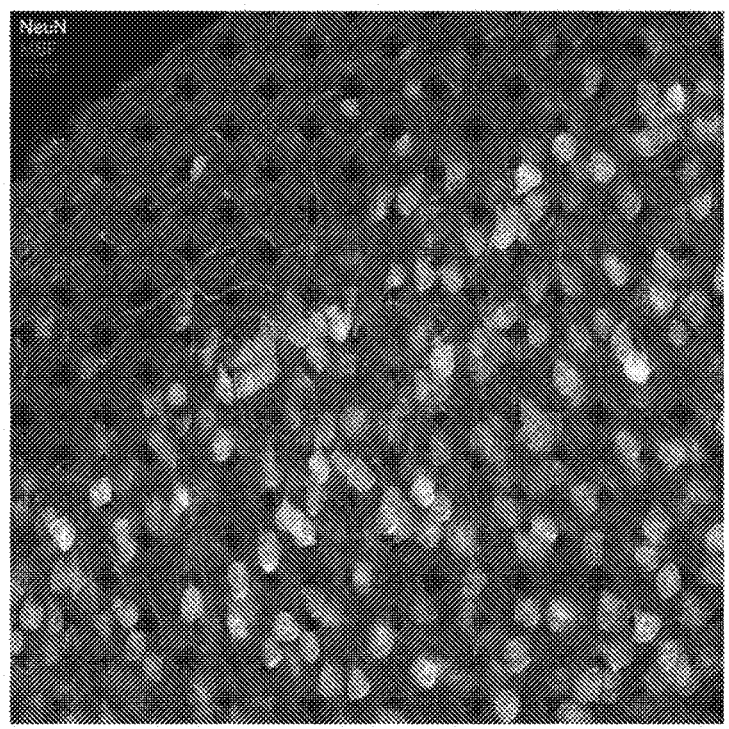
FIG. 5: Immunostaining of a 160-μm-thick mouse tissue hybridized into a hydrogel containing no sodium acrylate. The composition of hydrogel subunits used was 30% AA and 0.1% BA. MBP, myelin basic protein. GFP, green fluorescent protein. NeuN, neuronal nuclear protein.

A 160-µm-thick mouse brain coronal slice was embedded into a hydrogel with a formula of 30% acrylamide and 0.1% bis-acrylamide. The tissue size is smaller than a tissue-hydrogel hybrid containing 10% sodium acrylate and the pore size is expected to be smaller. Nevertheless, the tissue with no acrylate stained well with the same antibody incubation time, and also the antibody binding pattern and specificity were not changed (FIG. 5).

REFERENCES

1. Kasthuri, N. et al. Saturated reconstruction of a volume of neocortex. *Cell* 162, 648-661 (2015).
2. DeFelipe, J. From the connectome to the synaptome: an epic love story. *Science* 330, 1198-1201 (2010).
3. Oh, S. W. et al. A mesoscale connectome of the mouse brain. *Nature* 508, 207-214 (2014).
4. Kim, J. S. et al. Space-time wiring specificity supports direction selectivity in the retina. *Nature* 509, 331-336 (2014).
5. Lancaster, M. A. et al. Cerebral organoids model human brain development and microcephaly. *Nature* 501, 373-379 (2013).
6. Berglund, L. et al. A genecentric Human Protein Atlas for expression profiles based on antibodies. *Mol. Cell. Proteomics* 7, 2019-2027 (2008).
7. Sigal, Y. M., Speer, C. M., Babcock, H. P. & Zhuang, X. Mapping synaptic input fields of neurons with super-resolution imaging. *Cell* 163, 493-505 (2015).
8. Dani, A., Huang, B., Bergan, J., Dulac, C. & Zhuang, X. Superresolution imaging of chemical synapses in the brain. *Neuron* 68, 843-856 (2010).
9. Lakadamyali, M., Babcock, H., Bates, M., Zhuang, X. & Lichtman, J. 3D multicolor super-resolution imaging offers improved accuracy in neuron tracing. *PLoS One* 7, e30826 (2012).
10. Uhlen, M. et al. Towards a knowledge-based human protein atlas. *Nat. Biotechnol.* 28, 1248-1250 (2010).
11. Micheva, K. D. & Bruchez, M. P. The gain in brain: novel imaging techniques and multiplexed proteomic imaging of brain tissue ultrastructure. *Curr. Opin. Neurobiol.* 22, 94-100 (2012).

12. Dodt, H.-U. et al. Ultramicroscopy: three-dimensional visualization of neuronal networks in the whole mouse brain. *Nat. Methods* 4, 331-336 (2007).
13. Richardson, D. S. & Lichtman, J. W. Clarifying Tissue Clearing. *Cell* 162, 246-257 (2015).
14. Kay, K. R. et al. Studying synapses in human brain with array tomography and electron microscopy. *Nat. Protoc.* 8, 1366-1380 (2013).
15. Denk, W. & Horstmann, H. Serial block-face scanning electron microscopy to reconstruct three-dimensional tissue nanostructure. *PLoS Biol.* 2, e329 (2004).
16. Micheva, K. D. & Smith, S. J. Array tomography: a new tool for imaging the molecular architecture and ultrastructure of neural circuits. *Neuron* 55, 25-36 (2007).
17. Schubert, W. et al. Analyzing proteome topology and function by automated multidimensional fluorescence microscopy. *Nat. Biotechnol.* 24, 1270-1278 (2006).
18. Anderson, J. R. et al. A computational framework for ultrastructural mapping of neural circuitry. *PLoS Biol.* 7, e1000074 (2009).
19. Chung, K. & Deisseroth, K. CLARITY for mapping the nervous system. *Nat. Methods* 10, 508-513 (2013).
20. Puchtler, H. & Meloan, S. N. On the chemistry of formaldehyde fixation and its effects on immunohistochemical reactions. *Histochemistry* 82, 201-204 (1985).
21. Sung, H.-W., Hsu, H.-L., Shih, C.-C. & Lin, D.-S. Cross-linking characteristics of biological tissues fixed with monofunctional or multifunctional epoxy compounds. Biomaterials 17, 1405-1410 (1996).
22. Uhlen, M. & Ponten, F. Antibody-based proteomics for human tissue profiling. *Mol. Cell. Proteomics* 4, 384-393 (2005).
23. Kosaka, T. & Hama, K. Three-dimensional structure of astrocytes in the rat dentate gyrus. *J. Comp. Neurol.* 249, 242-260 (1986).
24. Khakh, B. S. & Sofroniew, M. V. Diversity of astrocyte functions and phenotypes in neural circuits. *Nat. Neurosci.* 18, 942-952 (2015).
25. Kasthuri, N. & Lichtman, J. W. The rise of the 'projectome'. *Nat. Methods* 4, 307-308 (2007).
26. Hell, S. W. & Wichmann, J. Breaking the diffraction resolution limit by stimulated emission: stimulated-emission-depletion fluorescence microscopy. *Opt. Lett.* 19, 780-782 (1994).
27. Betzig, E. et al. Imaging intracellular fluorescent proteins at nanometer resolution. *Science* 313, 1642-1645 (2006).
28. Chen, F., Tillberg, P. W. & Boyden, E. S. Expansion microscopy. *Science* 347, 543-548 (2015).
29. Feng, G. et al. Imaging neuronal subsets in transgenic mice expressing multiple spectral variants of GFP. *Neuron* 28, 41-51 (2000).
30. Tomer, R., Ye, L., Hsueh, B. & Deisseroth, K. Advanced CLARITY for rapid and high-resolution imaging of intact tissues. *Nat. Protoc.* 9, 1682-1697 (2014).
31. Ragan, T. et al. Serial two-photon tomography for automated ex vivo mouse brain imaging. *Nat. Methods* 9, 255-258 (2012).
32. Schindelin, J. et al. Fiji: an open-source platform for biological-image analysis. Nat. Methods 9, 676-682 (2012).
33. Kim, S.-Y. et al. Stochastic electrotransport selectively enhances the transport of highly electromobile molecules. *Proc. Natl Acad. Sci. USA*, doi: 10.1073/pnas.1510133112 (2 Nov. 2015).

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for preserving a tissue comprising:
   perfusing or incubating a tissue with hydrogel subunits,
   inducing polymerization of the hydrogel subunits under conditions comprising a concentration of hydrogel subunits that ranges from 25-80% weight/volume, and
   denaturing and/or dissociating biomolecules in the tissue, thereby forming a size-adjustable tissue-hydrogel hybrid,
   wherein the hydrogel subunits are acrylamide monomers.

2. The method of claim 1, wherein the tissue is perfused or incubated under conditions that minimize inter- or intra-tissue binding.

3. The method of claim 1, wherein the tissue is cultured cells.

4. The method of claim 1, wherein the concentration of hydrogel subunits ranges from 30-70%, 30-80%, or 40-80%.

5. The method of claim 1, wherein the tissue is perfused or incubated with hydrogel subunits and a fixative.

6. The method of claim 1, wherein denaturing and/or dissociating biomolecules comprises contacting the tissue with a detergent, incubating at high temperature, mechanical dissociation, or sonication.

7. The method of claim 1, wherein the tissue-hydrogel hybrid is reversibly and proportionally size-adjustable in three dimensions.

8. The method of claim 1, further comprising reversibly size-adjusting the tissue-hydrogel hybrid.

9. The method of claim 8, wherein reversibly size-adjusting the tissue-hydrogel hybrid comprises contacting the tissue-hydrogel hybrid with an aqueous solution or an aqueous saline solution.

10. The method of claim 1, wherein the tissue has been perfused and fixed with fixative prior to being incubated with hydrogel subunits.

11. The method of claim 1, wherein the concentration of hydrogel subunits is about 30%.

12. A method of producing a size-adjustable tissue-hydrogel hybrid comprising:
    perfusing a tissue with a concentration of hydrogel subunits under conditions that minimize inter- or intra-tissue bonding, wherein said conditions comprise modulating the concentration of hydrogel subunits to be between 25-80% weight/volume,
    inducing hybridization of the hydrogel subunits and tissue thereby forming a tissue-hydrogel hybrid, and
    denaturing and/or dissociating biomolecules in the tissue-hydrogel hybrid, thereby forming a size-adjustable tissue-hydrogel hybrid,
    wherein the hydrogel subunits are acrylamide monomers.

* * * * *